(12) United States Patent
Youle et al.

(10) Patent No.: US 6,737,511 B1
(45) Date of Patent: May 18, 2004

(54) RECEPTOR-MEDIATED UPTAKE OF AN EXTRACELLULAR BCL-$X_L$ FUSION PROTEIN INHIBITS APOPTOSIS

(75) Inventors: Richard J. Youle, Chevy Chase, MD (US); Liu Xiuhuai, Rockville, MD (US); R. John Collier, Wellesley, MA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/639,245

(22) Filed: Aug. 15, 2000

Related U.S. Application Data
(60) Provisional application No. 60/149,220, filed on Aug. 16, 1999.

(51) Int. Cl.[7] ............................................... C07K 14/00
(52) U.S. Cl. ................... 530/350; 530/351; 530/387.3; 530/387.7; 530/388.1; 530/388.8; 435/69.1; 435/69.5; 435/69.7; 435/71.3; 424/134.1; 424/138.1; 424/141.1; 424/236.1; 424/238.1
(58) Field of Search ................................ 530/350, 351, 530/387.3, 387.7, 388.1, 388.8; 435/69.1, 69.5, 69.7, 71.3; 424/134.1, 138.1, 141.1, 236.1, 238.1

(56) References Cited

U.S. PATENT DOCUMENTS

| | | |
|---|---|---|
| 5,080,898 A | 1/1992 | Murphy |
| 5,646,008 A | 7/1997 | Thompson et al. |
| 5,677,274 A | 10/1997 | Leppla et al. |
| 5,703,039 A | 12/1997 | Williams et al. |
| 5,763,250 A | 6/1998 | Williams et al. |
| 5,770,443 A | 6/1998 | Kiefer et al. |
| 5,789,201 A | 8/1998 | Guastella |
| 5,792,458 A | 8/1998 | Johnson et al. |
| 5,804,604 A | 9/1998 | Frankel et al. |
| 5,821,082 A | 10/1998 | Chinnadurai |
| 5,834,209 A | 11/1998 | Korsmeyer |
| 5,856,171 A | 1/1999 | Korsmeyer |
| 5,856,445 A | 1/1999 | Korsmeyer |
| 5,858,678 A | 1/1999 | Chinnadurai |
| 5,863,891 A | 1/1999 | Williams et al. |
| 5,932,471 A | 8/1999 | Williams et al. |
| 5,965,406 A | 10/1999 | Murphy |
| 5,965,703 A | 10/1999 | Horne et al. |
| 6,017,735 A | 1/2000 | O'Hare et al. |
| 6,022,720 A | 2/2000 | Martinou et al. |
| 6,022,950 A | 2/2000 | Murphy |
| 6,086,900 A * | 7/2000 | Draper .................... 424/282.1 |

FOREIGN PATENT DOCUMENTS

| | | |
|---|---|---|
| WO | WO 94/18332 | 8/1994 |
| WO | WO 97/23236 * | 7/1997 |
| WO | WO 97/41227 | 11/1997 |
| WO | WO 98/12328 | 3/1998 |
| WO | WO 98/17682 | 4/1998 |
| WO | WO 98/32866 | 7/1998 |
| WO | WO 99/16787 | 4/1999 |
| WO | WO 00/45128 | 9/1999 |

OTHER PUBLICATIONS

Fulton et al., Fed Proc 46 (4):1507, 1987.*
Benet et al., pp. 3–32, in The Pharmacological Basis of Therapeutics, 8th ed., McGraw–Hill, New York, 1990.*
Seaver, S., Genetic Engineering News 14/14:10 & 21, Aug. 1994.*
Burgess et al. Journal of Cell Biology, 1990, 11: 2129–2138.*
Gura. Science, 1997, 278:1041–1042.*
Jain. Sci. Am., 1994, 271:58–65.*
Curti. Crit. Rev. in Oncology/Hematology, 1993, 14:29–39.*
Hartwell et al. Science, 1997, 278:1064–1068.*
Ezzell. J. NIH Res, 1995, 7:46–49.*
Spitler. Cancer Biotherapy, 1995, 10:1–3.*
Boon. Adv Can Res, 1992, 58:177–210.*
Lazar et al. Molecular and Cell Biology, 1988: 8: 1247–1252.*
Tao. et al. The Journal of Immunology, 1989, 143(8): 2595–2601.*
Gillies et al. Human Antibodies and Hybridomas, 1990, 1(1): 47–54.*
Oltvai et al, 1994, Cell, 79: 189–192.*
Drexler et al (Leukemia and Lymphoma, 1993, 9:1–25).*
Embleton et al (Immunol Ser, 1984, 23:181–207).*
Hsu (in Tissue Culture Methods and Applications, Kruse and Patterson, Eds, 1973, Academic Press, NY, see abstract, p. 764.*
Freshney (Culture of Animal Cells, A Manual of Basic Technique, Alan R. Liss, Inc., 1983, New York, p4).*
Dermer (Bio/Technology, 1994, 12:320).*
Adams et al., "The Bcl–2 Protein Family: Arbiters of Cell Survival," *Science* 281:1322–1326, 1998.
Aqeilan et al., "Interleukin 2–Bax: a novel prototype of human chimeric proteins for targeted therapy," *FEBS Lett.* 457:271–276, 1999 (abstract only).
Ashkenazi et al., "Death Receptors: Signaling and Modulation," *Science* 281:1305–1308, 1998.
Barinaga, "Stroke–Damaged Neurons May Commit Cellular Suicide," *Science* 281:1302–1303, 1998.
Barinaga, "Is Apoptosis Key in Alzheimer's Disease?" *Science* 281:1303–1304, 1998.

(List continued on next page.)

*Primary Examiner*—Susan Ungar
*Assistant Examiner*—Minh Tam Davis
(74) *Attorney, Agent, or Firm*—Klarquist Sparkman, LLP

(57) ABSTRACT

Apoptosis-modifying fusion polypeptides, and the corresponding nucleic acid molecules, are disclosed. Pharmaceutical compositions comprising these polypeptides, and the use of these polypeptides to modify apoptosis are also provided.

12 Claims, 13 Drawing Sheets

OTHER PUBLICATIONS

Boise et al., "bcl–x, a bcl–2–Related Gene That Functions as a Dominant Regulator of Apoptotic Cell Death," *Cell* 74:597–608, 1993.

Chen et al., "bcl–2 is expressed in neurons that survive focal ischemia in the rat," *Neuroreport* 6:394–398, 1995 (abstract only).

Cheng et al., "Bax–Independent inhibition of apoptosis by Bcl–$X_L$," *Nature* 379:554–556, 1996.

Choe et al., "The crystal structure of diptheria toxin," *Nature* 357:216–222, 1992.

Coll–Fresno et al., "Cytotoxic activity of a diptheria toxin/FGF6 mototoxin on human tumour cell lines," *Oncogene* 14:243–247, 1997 (abstract only).

Datta et al., "Akt Phosphorylation of BAD Couples Survival Signals to the Cell–Intrinsic Death Machinery," *Cell* 91:231–241, 1997.

Elliott et al., "Intracellular trafficking and protein delivery by a herpesvirus structural protein," *Cell* 88:223–233, 1997 (abstract only).

Evan et al., "A Matter of Life and Cell Death," *Science* 281:1371–1322, 1998.

Farlie et al., "bcl–2 transgene expression can protect neurons against developmental and induced cell death," *Proc. Natl. Acad. Sci. USA* 92:4397–4401, 1995.

Frankel et al., "Modulation of the Apoptotic Response of Human Myeloid Leukemia Cells to a Diptheria Toxin Granulocyte–Macrophage Colony–Stimulating Factor Fusion Protein," *Blood* 90:3654–3661, 1997.

Froesch et al., "Inhibition of p53 Transcriptional Activity by Bcl–2 Requires Its Membrane–anchoring Domain," *J. Biol. Chem.* 274:6469–6475, 1999.

Gross et al., "Enforced dimerization of BAX results in its translocation, mitochondrial dysfunction and apoptosis," *EMBO J* 17:3878–3885, 1998 (abstract only).

Hengartner, "Death by Crowd Control," *Science* 281:1298–1304, 1998.

Johnson et al. "The role of proline 345 in diptheria toxin translocation," *J. Biol. Chem.* 268:3514–3519, 1993 (abstract only.

Laske et al., "Tumor regression with regional distribution of the targeted toxin TF–CRM107 in patients with malignant brain tumors," *Nat. Med.* 3:1362–1368, 1997 (abstract only).

Martinou et al., "Overexpression of BCL–2 in transgenic mice protects neurons from naturally occurring cell death and experimental ischemia," *Neuron* 13:1017–1030, 1994 (abstract only).

Matsuyama et al., "Cytoprotection by Bcl–2 Requires the Pore–forming α5 and α6 Helices," *J. Biol. Chem.* 273:30995–31001, 1998.

Miller et al., "Apoptosis," *Science* 281:1301, 1998.

Muchmore et al., "X–ray and NMR structure of human Bcl–$X_L$, an inhibitor of programmed cell death," *Nature* 381:335–341, 1996.

Negro, "Synthesis and cytotoxic profile of a diptheria toxin––neurotrophin–4 chimera," *J. Neurochem.* 68:554–563, 1997 (abstract only).

Oltval et al., "Bcl–2 Heterodimerizes In Vivo with a Conserved Homolog, Bax, That Accelerates Programmed Cell Death," *Cell* 74:609–619, 1993.

Parker et al., "Rendering a membrane protein soluble in water: a common packing motif in bacterial protein toxins," *TIBS* 18:391–395, 1993.

Perentesis et al., "Induction of Apoptosis in Multidrug–resistant and Radiation–resistant Acute Myeloid Leukemia Cells by a Recombinant Fusion Toxin Directed against the Human Granulocyte Macrophage Colony–stimulating Factor Receptor," *Clin. Cancer Res.* 3:347–355, 1997 (abstract only).

Perlman et al., "Bcl–2 Expression in synovial Fibroblasts Is Essential for Maintaining Mitochondrial Homeostasis and Cell Viability," *J. Immunol.* 164:5227–5235, 2000 (abstract only).

Rubin, "Neuronal cell death: when, why and how," *British Medical Bulletin* 53:617–631, 1997.

Schendel et al., "Channel formation by antiapoptotic protein Bcl–2," *Proc. Natl. Acad. Sci. USA* 94:5113–5118, 1997.

Schlesinger et al., "Comparison of the ion channel characteristics of proapoptotic BAX and antipoptotic BCL–2," *Proc Natl Acad Sci USA* 94:11357–11362, 1997 (abstract only).

Williams et al., "Diptheria toxin receptor binding domain substitution with interleukin–2: genetic construction and properties of a diptheria toxin–related interleukin–2 fusion protein," *Protein Eng* 1:493–498, 1987 (abstract only).

Williams et al., "Molecular Regulation of Apoptosis: Genetic Controls on Cell Death," *Cell* 74:777–779, 1993.

Yang et al., "Bad, a Heterodimeric Partner for Bcl–$X_L$ and Bcl–2, Displaces Bax and Promotes Cell Death," *Cell* 80:285–291, 1995.

Zha et al., "BH3 Domain of BAD Is Required for Heterodimerization with BCL–$X_L$ and Pro–apoptotic Activity," *The Journal of Biological Chemistry* 272:24101–24104, 1997.

Zha et al., "Serine Phosphorylation of Death Agonist BAD in Response to Survival Factor Results in Binding to 14–3–3 Not BCL–$X_L$," *Cell* 87:619–628, 1996.

Liu et al., "Receptor–mediated uptake of an extracellular Bcl–$x_L$ fusion protein inhibits apoptosis," *Proc. Natl. Acad. Sci. USA* 96:9563–9567, Aug. 1999.

Newton and Strasser, "The Bcl–2 family and cell death regulation," *Curr. Opin. Genet. Dev.* 8(1):68–75, 1998.

* cited by examiner

Lethal factor (LF)

LF(1-255) — Nde I ... (arrows)
Bcl-X$_L$(1-209) — Xho I

LF(1-255) + Bcl-X$_L$(1-209)
→ LFn-Bcl-X$_L$ in pET15b

SEQUENCE LISTING

```
<160> NUMBER OF SEQ ID NOS: 8

<210> SEQ ID NO 1
<211> LENGTH: 1236
<212> TYPE: DNA
<213> ORGANISM: Artificial Sequence
<220> FEATURE:
<223> OTHER INFORMATION: Description of Artificial Sequence: genetic
      fusion
<221> NAME/KEY: CDS
<222> LOCATION: (1)..(1236)

<400> SEQUENCE: 1 atg ggc cat cat cat cat cat cat cat cat cac agc agc ggc cat        48
Met Gly His His His His His His His His His Ser Ser Gly His
  1               5                  10                  15 atc gaa ggt cgt atg tct cag agc aac cgg gag ctg gtg gtt gac ttt    96
Ile Glu Gly Arg Met Ser Gln Ser Asn Arg Glu Leu Val Val Asp Phe
             20                  25                  30 ctc tcc tac aag ctt tcc cag aaa gga tac agc tgg agt cag ttt agt   144
Leu Ser Tyr Lys Leu Ser Gln Lys Gly Tyr Ser Trp Ser Gln Phe Ser
```

```
                           35                      40                       45
gat gtg gaa gag aac agg act gag gcc cca gaa ggg act gaa tcg gag    192
Asp Val Glu Glu Asn Arg Thr Glu Ala Pro Glu Gly Thr Glu Ser Glu
     50                      55                       60 atg gag acc ccc agt gcc atc aat ggc aac cca tcc tgg cac ctg gca    240
Met Glu Thr Pro Ser Ala Ile Asn Gly Asn Pro Ser Trp His Leu Ala
 65                      70                      75                  80 gac agc ccc gcg gtg aat gga gcc act gcg cac agc agc agt ttg gat    288
Asp Ser Pro Ala Val Asn Gly Ala Thr Ala His Ser Ser Ser Leu Asp
                     85                      90                      95 gcc cgg gag gtg atc ccc atg gca gca gta aag caa gcg ctg agg gag    336
Ala Arg Glu Val Ile Pro Met Ala Ala Val Lys Gln Ala Leu Arg Glu
                         100                     105                     110 gca ggc gac gag ttt gaa ctg cgg tac cgg cgg gca ttc agt gac ctg    384
Ala Gly Asp Glu Phe Glu Leu Arg Tyr Arg Arg Ala Phe Ser Asp Leu
             115                     120                     125 aca tcc cag ctc cac atc acc cca ggg aca gca tat cag agc ttt gaa    432
Thr Ser Gln Leu His Ile Thr Pro Gly Thr Ala Tyr Gln Ser Phe Glu
 130                     135                     140 cag gta gtg aat gaa ctc ttc cgg gat ggg gta aac tgg ggt cgc att    480
Gln Val Val Asn Glu Leu Phe Arg Asp Gly Val Asn Trp Gly Arg Ile
145                     150                     155                     160 gtg gcc ttt ttc tcc ttc ggc ggg gca ctg tgc gtg gaa agc gta gac    528
Val Ala Phe Phe Ser Phe Gly Gly Ala Leu Cys Val Glu Ser Val Asp
                         165                     170                     175 aag gag atg cag gta ttg gtg agt cgg atc gca gct tgg atg gcc act    576
Lys Glu Met Gln Val Leu Val Ser Arg Ile Ala Ala Trp Met Ala Thr
                 180                     185                     190 tac ctg aat gac cac cta gag cct tgg atc cag gag aac ggc ggc tgg    624
Tyr Leu Asn Asp His Leu Glu Pro Trp Ile Gln Glu Asn Gly Gly Trp
             195                     200                     205 gat act ttt gtg gaa ctc tat ggg aac aat gca gca gcc gag agc cga    672
Asp Thr Phe Val Glu Leu Tyr Gly Asn Asn Ala Ala Ala Glu Ser Arg
 210                     215                     220 aag ggc cag gaa cgc ttc aac cgc tgg ttc ctg acg ggc atg act gtg    720
Lys Gly Gln Glu Arg Phe Asn Arg Trp Phe Leu Thr Gly Met Thr Val
225                     230                     235                     240 gcc ggc gtg gtt ctg ctg ggc tca ctc ttc agt cgg aaa gcg tat tct    768
Ala Gly Val Val Leu Leu Gly Ser Leu Phe Ser Arg Lys Ala Tyr Ser
                         245                     250                     255 gcg gcc gcg cat aaa acg caa cca ttt ctt cat gac ggg tat gct gtc    816
Ala Ala Ala His Lys Thr Gln Pro Phe Leu His Asp Gly Tyr Ala Val
                 260                     265                     270 agt tgg aac act gtt gaa gat tcg ata atc cga act ggt ttt caa ggg    864
Ser Trp Asn Thr Val Glu Asp Ser Ile Ile Arg Thr Gly Phe Gln Gly
             275                     280                     285 gag agt ggg cac gac ata aaa att act gct gaa aat acc ccg ctt cca    912
Glu Ser Gly His Asp Ile Lys Ile Thr Ala Glu Asn Thr Pro Leu Pro
 290                     295                     300 atc gcg ggt gtc cta cta ccg act att cct gga aag ctg gac gtt aat    960
Ile Ala Gly Val Leu Leu Pro Thr Ile Pro Gly Lys Leu Asp Val Asn
305                     310                     315                     320 aag tcc aag act cat att tcc gta aat ggt cgg aaa ata agg atg cgt   1008
Lys Ser Lys Thr His Ile Ser Val Asn Gly Arg Lys Ile Arg Met Arg
                         325                     330                     335 tgc aga gct ata gac ggt gat gta act ttt tgt cgc cct aaa tct cct   1056
Cys Arg Ala Ile Asp Gly Asp Val Thr Phe Cys Arg Pro Lys Ser Pro
                 340                     345                     350 gtt tat gtt ggt aat ggt gtg cat gcg aat ctt cac gtg gca ttt cac   1104
```

```
                Val Tyr Val Gly Asn Gly Val His Ala Asn Leu His Val Ala Phe His
                        355                 360                 365 aga agc agc tcg gag aaa att cat tct aat gaa att tcg tcg gat tcc        1152
Arg Ser Ser Ser Glu Lys Ile His Ser Asn Glu Ile Ser Ser Asp Ser
370                 375                 380 ata ggc gtt ctt ggg tac cag aaa aca gta gat cac acc aag gtt aat        1200
Ile Gly Val Leu Gly Tyr Gln Lys Thr Val Asp His Thr Lys Val Asn
385                 390                 395                 400 tct aag cta tcg cta ttt ttt gaa atc aaa agc tga                        1236
Ser Lys Leu Ser Leu Phe Phe Glu Ile Lys Ser
                405                 410

<210> SEQ ID NO 2
<211> LENGTH: 411
<212> TYPE: PRT
<213> ORGANISM: Artificial Sequence
<220> FEATURE:
<223> OTHER INFORMATION: Description of Artificial Sequence: genetic
      fusion

<400> SEQUENCE: 2

Met Gly His His His His His His His His Ser Ser Gly His
 1               5                  10                  15

Ile Glu Gly Arg Met Ser Gln Ser Asn Arg Glu Leu Val Val Asp Phe
            20                  25                  30

Leu Ser Tyr Lys Leu Ser Gln Lys Gly Tyr Ser Trp Ser Gln Phe Ser
        35                  40                  45

Asp Val Glu Glu Asn Arg Thr Glu Ala Pro Glu Gly Thr Glu Ser Glu
    50                  55                  60

Met Glu Thr Pro Ser Ala Ile Asn Gly Asn Pro Ser Trp His Leu Ala
65                  70                  75                  80

Asp Ser Pro Ala Val Asn Gly Ala Thr Ala His Ser Ser Ser Leu Asp
                85                  90                  95

Ala Arg Glu Val Ile Pro Met Ala Ala Val Lys Gln Ala Leu Arg Glu
            100                 105                 110

Ala Gly Asp Glu Phe Glu Leu Arg Tyr Arg Arg Ala Phe Ser Asp Leu
        115                 120                 125

Thr Ser Gln Leu His Ile Thr Pro Gly Thr Ala Tyr Gln Ser Phe Glu
    130                 135                 140

Gln Val Val Asn Glu Leu Phe Arg Asp Gly Val Asn Trp Gly Arg Ile
145                 150                 155                 160

Val Ala Phe Phe Ser Phe Gly Gly Ala Leu Cys Val Glu Ser Val Asp
                165                 170                 175

Lys Glu Met Gln Val Leu Val Ser Arg Ile Ala Ala Trp Met Ala Thr
            180                 185                 190

Tyr Leu Asn Asp His Leu Glu Pro Trp Ile Gln Glu Asn Gly Gly Trp
        195                 200                 205

Asp Thr Phe Val Glu Leu Tyr Gly Asn Asn Ala Ala Ala Glu Ser Arg
    210                 215                 220

Lys Gly Gln Glu Arg Phe Asn Arg Trp Phe Leu Thr Gly Met Thr Val
225                 230                 235                 240

Ala Gly Val Val Leu Leu Gly Ser Leu Phe Ser Arg Lys Ala Tyr Ser
                245                 250                 255

Ala Ala Ala His Lys Thr Gln Pro Phe Leu His Asp Gly Tyr Ala Val
            260                 265                 270

Ser Trp Asn Thr Val Glu Asp Ser Ile Ile Arg Thr Gly Phe Gln Gly
        275                 280                 285
```

```
Glu Ser Gly His Asp Ile Lys Ile Thr Ala Glu Asn Thr Pro Leu Pro
    290                 295                 300

Ile Ala Gly Val Leu Leu Pro Thr Ile Pro Gly Lys Leu Asp Val Asn
305                 310                 315                 320

Lys Ser Lys Thr His Ile Ser Val Asn Gly Arg Lys Ile Arg Met Arg
                325                 330                 335

Cys Arg Ala Ile Asp Gly Asp Val Thr Phe Cys Arg Pro Lys Ser Pro
                340                 345                 350

Val Tyr Val Gly Asn Gly Val His Ala Asn Leu His Val Ala Phe His
                355                 360                 365

Arg Ser Ser Ser Glu Lys Ile His Ser Asn Glu Ile Ser Ser Asp Ser
    370                 375                 380

Ile Gly Val Leu Gly Tyr Gln Lys Thr Val Asp His Thr Lys Val Asn
385                 390                 395                 400

Ser Lys Leu Ser Leu Phe Phe Glu Ile Lys Ser
                405                 410

<210> SEQ ID NO 3
<211> LENGTH: 1704
<212> TYPE: DNA
<213> ORGANISM: Artificial Sequence
<220> FEATURE:
<223> OTHER INFORMATION: Description of Artificial Sequence: genetic
      fusion
<221> NAME/KEY: CDS
<222> LOCATION: (1)..(1704)

<400> SEQUENCE: 3 atg ggc cat cat cat cat cat cat cat cat cac agc agc ggc cat        48
Met Gly His His His His His His His His His Ser Ser Gly His
 1               5                   10                  15 atc gaa ggt cgt cat atg gga acc cca aag cag ccc tcg ctg gct cct    96
Ile Glu Gly Arg His Met Gly Thr Pro Lys Gln Pro Ser Leu Ala Pro
                20                  25                  30 gca cac gcc cta ggc ttg agg aag tcc gat ccc gga atc cgg agc ctg   144
Ala His Ala Leu Gly Leu Arg Lys Ser Asp Pro Gly Ile Arg Ser Leu
             35                  40                  45 ggg agc gac gcg gga gga agg cgg tgg aga cca gca gcc cag agt atg   192
Gly Ser Asp Ala Gly Gly Arg Arg Trp Arg Pro Ala Ala Gln Ser Met
         50                  55                  60 ttc cag atc cca gag ttt gag ccg agt gag cag gaa gac gct agt gct   240
Phe Gln Ile Pro Glu Phe Glu Pro Ser Glu Gln Glu Asp Ala Ser Ala
 65                  70                  75                  80 aca gat agg ggc ctg ggc cct agc ctc act gag gac cag cca ggt ccc   288
Thr Asp Arg Gly Leu Gly Pro Ser Leu Thr Glu Asp Gln Pro Gly Pro
                 85                  90                  95 tac ctg gcc cca ggt ctc ctg ggg agc aac att cat cag cag gga cgg   336
Tyr Leu Ala Pro Gly Leu Leu Gly Ser Asn Ile His Gln Gln Gly Arg
            100                 105                 110 gca gcc acc aac agt cat cat gga ggc gca ggg gct atg gag act cgg   384
Ala Ala Thr Asn Ser His His Gly Gly Ala Gly Ala Met Glu Thr Arg
        115                 120                 125 agt cgc cac agt gcg tac cca gcg ggg acc gag gag gat gaa ggg atg   432
Ser Arg His Ser Ala Tyr Pro Ala Gly Thr Glu Glu Asp Glu Gly Met
    130                 135                 140 gag gag gag ctt agc cct ttt cga gga cgc tcg cgt gcg gct ccc ccc   480
Glu Glu Glu Leu Ser Pro Phe Arg Gly Arg Ser Arg Ala Ala Pro Pro
145                 150                 155                 160 aat ctc tgg gca gcg cag cgc tac ggc cgt gag ctc cga agg atg agc   528
```

```
                                                  -continued

Asn Leu Trp Ala Ala Gln Arg Tyr Gly Arg Glu Leu Arg Arg Met Ser
            165                 170                 175 gat gag ttt gag ggt tcc ttc aag gga ctt cct cgc cca aag agc gca      576
Asp Glu Phe Glu Gly Ser Phe Lys Gly Leu Pro Arg Pro Lys Ser Ala
        180                 185                 190 ggc act gca aca cag atg cga caa agc gcc ggc tgg acg cgc att atc      624
Gly Thr Ala Thr Gln Met Arg Gln Ser Ala Gly Trp Thr Arg Ile Ile
    195                 200                 205 cag tcc tgg tgg gat cga aac ttg ggc aaa gga ggc tcc acc ccc tcc      672
Gln Ser Trp Trp Asp Arg Asn Leu Gly Lys Gly Gly Ser Thr Pro Ser
210                 215                 220 cag tca gta ggt agc tca ttg tca tgc ata aat ctt gat tgg gat gtc      720
Gln Ser Val Gly Ser Ser Leu Ser Cys Ile Asn Leu Asp Trp Asp Val
225                 230                 235                 240 ata agg gat aaa act aag aca aag ata gag tct ttg aaa gag cat ggc      768
Ile Arg Asp Lys Thr Lys Thr Lys Ile Glu Ser Leu Lys Glu His Gly
            245                 250                 255 cct atc aaa aat aaa atg agc gaa agt ccc aat aaa aca gta tct gag      816
Pro Ile Lys Asn Lys Met Ser Glu Ser Pro Asn Lys Thr Val Ser Glu
        260                 265                 270 gaa aaa gct aaa caa tac cta gaa gaa ttt cat caa acg gca tta gag      864
Glu Lys Ala Lys Gln Tyr Leu Glu Glu Phe His Gln Thr Ala Leu Glu
    275                 280                 285 cat cct gaa ttg tca gaa ctt aaa acc gtt act ggg acc aat cct gta      912
His Pro Glu Leu Ser Glu Leu Lys Thr Val Thr Gly Thr Asn Pro Val
290                 295                 300 ttc gct ggg gct aac tat gcg gcg tgg gca gta aac gtt gcg caa gtt      960
Phe Ala Gly Ala Asn Tyr Ala Ala Trp Ala Val Asn Val Ala Gln Val
305                 310                 315                 320 atc gat agc gaa aca gct gat aat ttg gaa aag aca act gct gct ctt     1008
Ile Asp Ser Glu Thr Ala Asp Asn Leu Glu Lys Thr Thr Ala Ala Leu
            325                 330                 335 tcg ata ctt cct ggt atc ggt agc gta atg ggc att gca gac ggt gcc     1056
Ser Ile Leu Pro Gly Ile Gly Ser Val Met Gly Ile Ala Asp Gly Ala
        340                 345                 350 gtt cac cac aat aca gaa gag ata gtg gca caa tca ata gct tta tcg     1104
Val His His Asn Thr Glu Glu Ile Val Ala Gln Ser Ile Ala Leu Ser
    355                 360                 365 tct tta atg gtt gct caa gct att cca ttg gta gga gag cta gtt gat     1152
Ser Leu Met Val Ala Gln Ala Ile Pro Leu Val Gly Glu Leu Val Asp
370                 375                 380 att ggt ttc gct gca tat aat ttt gta gag agt att atc aat tta ttt     1200
Ile Gly Phe Ala Ala Tyr Asn Phe Val Glu Ser Ile Ile Asn Leu Phe
385                 390                 395                 400 caa gta gtt cat aat tcg tat aat cgt ccc gcg tat tct ccg ggg cat     1248
Gln Val Val His Asn Ser Tyr Asn Arg Pro Ala Tyr Ser Pro Gly His
            405                 410                 415 aaa acg caa cca ttt ctt cat gac ggg tat gct gtc agt tgg aac act     1296
Lys Thr Gln Pro Phe Leu His Asp Gly Tyr Ala Val Ser Trp Asn Thr
        420                 425                 430 gtt gaa gat tcg ata atc cga act ggt ttt caa ggg gag agt ggg cac     1344
Val Glu Asp Ser Ile Ile Arg Thr Gly Phe Gln Gly Glu Ser Gly His
    435                 440                 445 gac ata aaa att act gct gaa aat acc ccg ctt cca atc gcg ggt gtc     1392
Asp Ile Lys Ile Thr Ala Glu Asn Thr Pro Leu Pro Ile Ala Gly Val
450                 455                 460 cta cta ccg act att cct gga aag ctg gac gtt aat aag tcc aag act     1440
Leu Leu Pro Thr Ile Pro Gly Lys Leu Asp Val Asn Lys Ser Lys Thr
465                 470                 475                 480
```

```
cat att tcc gta aat ggt cgg aaa ata agg atg cgt tgc aga gct ata    1488
His Ile Ser Val Asn Gly Arg Lys Ile Arg Met Arg Cys Arg Ala Ile
                485                 490                 495 gac ggt gat gta act ttt tgt cgc cct aaa tct cct gtt tat gtt ggt    1536
Asp Gly Asp Val Thr Phe Cys Arg Pro Lys Ser Pro Val Tyr Val Gly
            500                 505                 510 aat ggt gtg cat gcg aat ctt cac gtg gca ttt cac aga agc agc tcg    1584
Asn Gly Val His Ala Asn Leu His Val Ala Phe His Arg Ser Ser Ser
        515                 520                 525 gag aaa att cat tct aat gaa att tcg tcg gat tcc ata ggc gtt ctt    1632
Glu Lys Ile His Ser Asn Glu Ile Ser Ser Asp Ser Ile Gly Val Leu
    530                 535                 540 ggg tac cag aaa aca gta gat cac acc aag gtt aat tct aag cta tcg    1680
Gly Tyr Gln Lys Thr Val Asp His Thr Lys Val Asn Ser Lys Leu Ser
545                 550                 555                 560 cta ttt ttt gaa atc aaa agc tga                                    1704
Leu Phe Phe Glu Ile Lys Ser
                565
```

<210> SEQ ID NO 4
<211> LENGTH: 567
<212> TYPE: PRT
<213> ORGANISM: Artificial Sequence
<220> FEATURE:
<223> OTHER INFORMATION: Description of Artificial Sequence: genetic fusion

<400> SEQUENCE: 4

```
Met Gly His His His His His His His His Ser Ser Gly His
1               5                   10                  15

Ile Glu Gly Arg His Met Gly Thr Pro Lys Gln Pro Ser Leu Ala Pro
                20                  25                  30

Ala His Ala Leu Gly Leu Arg Lys Ser Asp Pro Gly Ile Arg Ser Leu
            35                  40                  45

Gly Ser Asp Ala Gly Gly Arg Trp Arg Pro Ala Ala Gln Ser Met
        50                  55                  60

Phe Gln Ile Pro Glu Phe Glu Pro Ser Glu Gln Glu Asp Ala Ser Ala
65                  70                  75                  80

Thr Asp Arg Gly Leu Gly Pro Ser Leu Thr Glu Asp Gln Pro Gly Pro
                85                  90                  95

Tyr Leu Ala Pro Gly Leu Leu Gly Ser Asn Ile His Gln Gln Gly Arg
            100                 105                 110

Ala Ala Thr Asn Ser His His Gly Gly Ala Gly Ala Met Glu Thr Arg
        115                 120                 125

Ser Arg His Ser Ala Tyr Pro Ala Gly Thr Glu Asp Glu Gly Met
    130                 135                 140

Glu Glu Glu Leu Ser Pro Phe Arg Gly Ser Arg Ala Ala Pro Pro
145                 150                 155                 160

Asn Leu Trp Ala Ala Gln Arg Tyr Gly Arg Glu Leu Arg Arg Met Ser
                165                 170                 175

Asp Glu Phe Glu Gly Ser Phe Lys Gly Leu Pro Arg Pro Lys Ser Ala
            180                 185                 190

Gly Thr Ala Thr Gln Met Arg Gln Ser Ala Gly Trp Thr Arg Ile Ile
        195                 200                 205

Gln Ser Trp Trp Asp Arg Asn Leu Gly Lys Gly Ser Thr Pro Ser
    210                 215                 220

Gln Ser Val Gly Ser Ser Leu Ser Cys Ile Asn Leu Asp Trp Asp Val
225                 230                 235                 240
```

```
Ile Arg Asp Lys Thr Lys Thr Lys Ile Glu Ser Leu Lys Glu His Gly
                245                 250                 255
Pro Ile Lys Asn Lys Met Ser Glu Ser Pro Asn Lys Thr Val Ser Glu
            260                 265                 270
Glu Lys Ala Lys Gln Tyr Leu Glu Glu Phe His Gln Thr Ala Leu Glu
        275                 280                 285
His Pro Glu Leu Ser Glu Leu Lys Thr Val Thr Gly Thr Asn Pro Val
    290                 295                 300
Phe Ala Gly Ala Asn Tyr Ala Ala Trp Ala Val Asn Val Ala Gln Val
305                 310                 315                 320
Ile Asp Ser Glu Thr Ala Asp Asn Leu Glu Lys Thr Thr Ala Ala Leu
                325                 330                 335
Ser Ile Leu Pro Gly Ile Gly Ser Val Met Gly Ile Ala Asp Gly Ala
            340                 345                 350
Val His His Asn Thr Glu Glu Ile Val Ala Gln Ser Ile Ala Leu Ser
        355                 360                 365
Ser Leu Met Val Ala Gln Ala Ile Pro Leu Val Gly Glu Leu Val Asp
    370                 375                 380
Ile Gly Phe Ala Ala Tyr Asn Phe Val Glu Ser Ile Ile Asn Leu Phe
385                 390                 395                 400
Gln Val Val His Asn Ser Tyr Asn Arg Pro Ala Tyr Ser Pro Gly His
                405                 410                 415
Lys Thr Gln Pro Phe Leu His Asp Gly Tyr Ala Val Ser Trp Asn Thr
            420                 425                 430
Val Glu Asp Ser Ile Ile Arg Thr Gly Phe Gln Gly Glu Ser Gly His
        435                 440                 445
Asp Ile Lys Ile Thr Ala Glu Asn Thr Pro Leu Pro Ile Ala Gly Val
    450                 455                 460
Leu Leu Pro Thr Ile Pro Gly Lys Leu Asp Val Asn Lys Ser Lys Thr
465                 470                 475                 480
His Ile Ser Val Asn Gly Arg Lys Ile Arg Met Arg Cys Arg Ala Ile
                485                 490                 495
Asp Gly Asp Val Thr Phe Cys Arg Pro Lys Ser Pro Val Tyr Val Gly
            500                 505                 510
Asn Gly Val His Ala Asn Leu His Val Ala Phe His Arg Ser Ser Ser
        515                 520                 525
Glu Lys Ile His Ser Asn Glu Ile Ser Ser Asp Ser Ile Gly Val Leu
    530                 535                 540
Gly Tyr Gln Lys Thr Val Asp His Thr Lys Val Asn Ser Lys Leu Ser
545                 550                 555                 560
Leu Phe Phe Glu Ile Lys Ser
                565
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: oligonucleotide linker

<400> SEQUENCE: 5
gcgtattctg cggccgcg                                              18

<210> SEQ ID NO 6

-continued

```
<211> LENGTH: 6
<212> TYPE: PRT
<213> ORGANISM: Artificial Sequence
<220> FEATURE:
<223> OTHER INFORMATION: Description of Artificial Sequence:
      oligopeptide linker

<400> SEQUENCE: 6

Ala Tyr Ser Ala Ala Ala
 1               5

<210> SEQ ID NO 7
<211> LENGTH: 1455
<212> TYPE: DNA
<213> ORGANISM: Artificial Sequence
<220> FEATURE:
<223> OTHER INFORMATION: Description of Artificial Sequence: genetic
      fusion
<221> NAME/KEY: CDS
<222> LOCATION: (1)..(1455)

<400> SEQUENCE: 7 atg ggc agc agc cat cat cat cat cat cac agc agc ggc ctg gtg ccg      48
Met Gly Ser Ser His His His His His His Ser Ser Gly Leu Val Pro
 1               5                  10                  15 cgc ggc agc cat atg gcg ggc ggt cat ggt gat gta ggt atg cac gta      96
Arg Gly Ser His Met Ala Gly Gly His Gly Asp Val Gly Met His Val
                20                  25                  30 aaa gag aaa gag aaa aat aaa gat gag aat aag aga aaa gat gaa gaa     144
Lys Glu Lys Glu Lys Asn Lys Asp Glu Asn Lys Arg Lys Asp Glu Glu
            35                  40                  45 cga aat aaa aca cag gaa gag cat tta aag gaa atc atg aaa cac att     192
Arg Asn Lys Thr Gln Glu Glu His Leu Lys Glu Ile Met Lys His Ile
        50                  55                  60 gta aaa ata gaa gta aaa ggg gag gaa gct gtt aaa aaa gag gca gca     240
Val Lys Ile Glu Val Lys Gly Glu Glu Ala Val Lys Lys Glu Ala Ala
 65                  70                  75                  80 gaa aag cta ctt gag aaa gta cca tct gat gtt tta gag atg tat aaa     288
Glu Lys Leu Leu Glu Lys Val Pro Ser Asp Val Leu Glu Met Tyr Lys
                 85                  90                  95 gca att gga gga aag ata tat att gtg gat ggt gat att aca aaa cat     336
Ala Ile Gly Gly Lys Ile Tyr Ile Val Asp Gly Asp Ile Thr Lys His
            100                 105                 110 ata tct tta gaa gca tta tct gaa gat aag aaa aaa ata aaa gac att     384
Ile Ser Leu Glu Ala Leu Ser Glu Asp Lys Lys Lys Ile Lys Asp Ile
        115                 120                 125 tat ggg aaa gat gct tta tta cat gaa cat tat gta tat gca aaa gaa     432
Tyr Gly Lys Asp Ala Leu Leu His Glu His Tyr Val Tyr Ala Lys Glu
    130                 135                 140 gga tat gaa ccc gta ctt gta atc caa tct tcg gaa gat tat gta gaa     480
Gly Tyr Glu Pro Val Leu Val Ile Gln Ser Ser Glu Asp Tyr Val Glu
145                 150                 155                 160 aat act gaa aag gca ctg aac gtt tat tat gaa ata ggt aag ata tta     528
Asn Thr Glu Lys Ala Leu Asn Val Tyr Tyr Glu Ile Gly Lys Ile Leu
                165                 170                 175 tca agg gat att tta agt aaa att aat caa cca tat cag aaa ttt tta     576
Ser Arg Asp Ile Leu Ser Lys Ile Asn Gln Pro Tyr Gln Lys Phe Leu
            180                 185                 190 gat gta tta aat acc att aaa aat gca tct gat tca gat gga caa gat     624
Asp Val Leu Asn Thr Ile Lys Asn Ala Ser Asp Ser Asp Gly Gln Asp
        195                 200                 205 ctt tta ttt act aat cag ctt aag gaa cat ccc aca gac ttt tct gta     672
Leu Leu Phe Thr Asn Gln Leu Lys Glu His Pro Thr Asp Phe Ser Val
```

```
                210                 215                 220
gaa ttc ttg gaa caa aat agc aat gag gta caa gaa gta ttt gcg aaa      720
Glu Phe Leu Glu Gln Asn Ser Asn Glu Val Gln Glu Val Phe Ala Lys
225                 230                 235                 240 gct ttt gca tat tat atc gag cca cag cat cgt gat gtt tta cag ctt      768
Ala Phe Ala Tyr Tyr Ile Glu Pro Gln His Arg Asp Val Leu Gln Leu
                245                 250                 255 tat gca ccg gaa gct ttt aat tac atg gat aaa ttt aac gaa caa gaa      816
Tyr Ala Pro Glu Ala Phe Asn Tyr Met Asp Lys Phe Asn Glu Gln Glu
            260                 265                 270 ata aat cta tcc atg tct cag agc aac cgg gag ctg gtg gtt gac ttt      864
Ile Asn Leu Ser Met Ser Gln Ser Asn Arg Glu Leu Val Val Asp Phe
        275                 280                 285 ctc tcc tac aag ctt tcc cag aaa gga tac agc tgg agt cag ttt agt      912
Leu Ser Tyr Lys Leu Ser Gln Lys Gly Tyr Ser Trp Ser Gln Phe Ser
    290                 295                 300 gat gtg gaa gag aac agg act gag gcc cca gaa ggg act gaa tcg gag      960
Asp Val Glu Glu Asn Arg Thr Glu Ala Pro Glu Gly Thr Glu Ser Glu
305                 310                 315                 320 atg gag acc ccc agt gcc atc aat ggc aac cca tcc tgg cac ctg gca     1008
Met Glu Thr Pro Ser Ala Ile Asn Gly Asn Pro Ser Trp His Leu Ala
                325                 330                 335 gac agc ccc gcg gtg aat gga gcc act gcg cac agc agc agt ttg gat     1056
Asp Ser Pro Ala Val Asn Gly Ala Thr Ala His Ser Ser Ser Leu Asp
            340                 345                 350 gcc cgg gag gtg atc ccc atg gca gca gta aag caa gcg ctg agg gag     1104
Ala Arg Glu Val Ile Pro Met Ala Ala Val Lys Gln Ala Leu Arg Glu
        355                 360                 365 gca ggc gac gag ttt gaa ctg cgg tac cgg cgg gca ttc agt gac ctg     1152
Ala Gly Asp Glu Phe Glu Leu Arg Tyr Arg Arg Ala Phe Ser Asp Leu
    370                 375                 380 aca tcc cag ctc cac atc acc cca ggg aca gca tat cag agc ttt gaa     1200
Thr Ser Gln Leu His Ile Thr Pro Gly Thr Ala Tyr Gln Ser Phe Glu
385                 390                 395                 400 cag gta gtg aat gaa ctc ttc cgg gat ggg gta aac tgg ggt cgc att     1248
Gln Val Val Asn Glu Leu Phe Arg Asp Gly Val Asn Trp Gly Arg Ile
                405                 410                 415 gtg gcc ttt ttc tcc ttc ggc ggg gca ctg tgc gtg gaa agc gta gac     1296
Val Ala Phe Phe Ser Phe Gly Gly Ala Leu Cys Val Glu Ser Val Asp
            420                 425                 430 aag gag atg cag gta ttg gtg agt cgg atc gca gct tgg atg gcc act     1344
Lys Glu Met Gln Val Leu Val Ser Arg Ile Ala Ala Trp Met Ala Thr
        435                 440                 445 tac ctg aat gac cac cta gag cct tgg atc cag gag aac ggc ggc tgg     1392
Tyr Leu Asn Asp His Leu Glu Pro Trp Ile Gln Glu Asn Gly Gly Trp
    450                 455                 460 gat act ttt gtg gaa ctc tat ggg aac aat gca gca gcc gag agc cga     1440
Asp Thr Phe Val Glu Leu Tyr Gly Asn Asn Ala Ala Ala Glu Ser Arg
465                 470                 475                 480 aag ggc cag gaa cgc                                                 1455
Lys Gly Gln Glu Arg
                485

<210> SEQ ID NO 8
<211> LENGTH: 485
<212> TYPE: PRT
<213> ORGANISM: Artificial Sequence
<220> FEATURE:
<223> OTHER INFORMATION: Description of Artificial Sequence: genetic
      fusion
```

-continued

<400> SEQUENCE: 8

```
Met Gly Ser Ser His His His His His His Ser Ser Gly Leu Val Pro
 1               5                  10                  15

Arg Gly Ser His Met Ala Gly Gly His Gly Asp Val Gly Met His Val
            20                  25                  30

Lys Glu Lys Glu Lys Asn Lys Asp Glu Asn Lys Arg Lys Asp Glu Glu
        35                  40                  45

Arg Asn Lys Thr Gln Glu Glu His Leu Lys Glu Ile Met Lys His Ile
    50                  55                  60

Val Lys Ile Glu Val Lys Gly Glu Glu Ala Val Lys Lys Glu Ala Ala
 65                  70                  75                  80

Glu Lys Leu Leu Glu Lys Val Pro Ser Asp Val Leu Glu Met Tyr Lys
                85                  90                  95

Ala Ile Gly Gly Lys Ile Tyr Ile Val Asp Gly Asp Ile Thr Lys His
            100                 105                 110

Ile Ser Leu Glu Ala Leu Ser Glu Asp Lys Lys Ile Lys Asp Ile
        115                 120                 125

Tyr Gly Lys Asp Ala Leu Leu His Glu His Tyr Val Tyr Ala Lys Glu
    130                 135                 140

Gly Tyr Glu Pro Val Leu Val Ile Gln Ser Ser Glu Asp Tyr Val Glu
145                 150                 155                 160

Asn Thr Glu Lys Ala Leu Asn Val Tyr Glu Ile Gly Lys Ile Leu
                165                 170                 175

Ser Arg Asp Ile Leu Ser Lys Ile Asn Gln Pro Tyr Gln Lys Phe Leu
            180                 185                 190

Asp Val Leu Asn Thr Ile Lys Asn Ala Ser Asp Ser Asp Gly Gln Asp
        195                 200                 205

Leu Leu Phe Thr Asn Gln Leu Lys Glu His Pro Thr Asp Phe Ser Val
    210                 215                 220

Glu Phe Leu Glu Gln Asn Ser Asn Glu Val Gln Glu Val Phe Ala Lys
225                 230                 235                 240

Ala Phe Ala Tyr Tyr Ile Glu Pro Gln His Arg Asp Val Leu Gln Leu
                245                 250                 255

Tyr Ala Pro Glu Ala Phe Asn Tyr Met Asp Lys Phe Asn Glu Gln Glu
            260                 265                 270

Ile Asn Leu Ser Met Ser Gln Ser Asn Arg Glu Leu Val Val Asp Phe
        275                 280                 285

Leu Ser Tyr Lys Leu Ser Gln Lys Gly Tyr Ser Trp Ser Gln Phe Ser
    290                 295                 300

Asp Val Glu Glu Asn Arg Thr Glu Ala Pro Glu Gly Thr Glu Ser Glu
305                 310                 315                 320

Met Glu Thr Pro Ser Ala Ile Asn Gly Asn Pro Ser Trp His Leu Ala
                325                 330                 335

Asp Ser Pro Ala Val Asn Gly Ala Thr Ala His Ser Ser Ser Leu Asp
            340                 345                 350

Ala Arg Glu Val Ile Pro Met Ala Ala Val Lys Gln Ala Leu Arg Glu
        355                 360                 365

Ala Gly Asp Glu Phe Glu Leu Arg Tyr Arg Arg Ala Phe Ser Asp Leu
    370                 375                 380

Thr Ser Gln Leu His Ile Thr Pro Gly Thr Ala Tyr Gln Ser Phe Glu
385                 390                 395                 400

Gln Val Val Asn Glu Leu Phe Arg Asp Gly Val Asn Trp Gly Arg Ile
                405                 410                 415
```

-continued

```
Val Ala Phe Phe Ser Phe Gly Gly Ala Leu Cys Val Glu Ser Val Asp
            420             425             430

Lys Glu Met Gln Val Leu Val Ser Arg Ile Ala Ala Trp Met Ala Thr
        435             440             445

Tyr Leu Asn Asp His Leu Glu Pro Trp Ile Gln Glu Asn Gly Gly Trp
    450             455             460

Asp Thr Phe Val Glu Leu Tyr Gly Asn Asn Ala Ala Ala Glu Ser Arg
465             470             475             480

Lys Gly Gln Glu Arg
                485
```

RECEPTOR-MEDIATED UPTAKE OF AN EXTRACELLULAR BCL-$X_L$ FUSION PROTEIN INHIBITS APOPTOSIS

RELATED APPLICATIONS

This application claims priority based on U.S. provisional application No. 60/149,220, filed Aug. 16, 1999, herein incorporated by reference in its entirety.

FIELD

This invention relates to modification of the apoptotic response of target cells, for instance target cells in a subject. More specifically, it relates to apoptosis-modifying fusion proteins with at least two domains, one of which targets the fusion protein to a target cell, and another of which modifies an apoptotic response of the target cell.

BACKGROUND

Tissue and cell homeostasis in multicellular organisms is largely influenced by apoptosis, the phenomenon of programmed cell death by which an intra- or extra-cellular trigger causes a cell to activate a biochemical "suicide" pathway. Morphological indicia of apoptosis include membrane blebbing, chromatin condensation and fragmentation, and formation of apoptotic bodies, all of which take place relatively early in the process of programmed cell death. Degradation of genomic DNA during apoptosis results in formation of characteristic, nucleosome sized DNA fragments; this degradation produces a diagnostic ~180 bp laddering pattern when analyzed by gel electrophoresis. A later step in the apoptotic process is degradation of the plasma membrane, rendering apoptotic cells leaky to various dyes (e.g., trypan blue and propidium iodide). Apoptotic cells are usually engulfed and destroyed early in the death process; thus, apoptosis tends not to be associated with inflammation caused by cytoplasm leakage, as is found in necrosis.

Various in vivo triggers can induce apoptosis; the paradigmatic trigger is a shortage of one or more necessary growth factors. Apoptosis plays a significant role in development of the neural system (reviewed in Cowan et al., Science 225:1258–1265, 1984; Davies, Development 101:185–208, 1987; Oppenheim, Annu. Rev. Neurosci. 14:453–501, 1991) and lymphoid system (reviewed in Blackman et al., Science 248:1335–1341, 1990; Rothenberg, Adv. Immunol. 51:85–214, 1992) of vertebrates. System development occurs through selective apoptotic extinction of certain cell populations.

In spite of much study, the molecular mechanisms of apoptosis are not fully elucidated. It does appear, however, that different apoptosis inducers may trigger different apoptotic pathways. For instance, certain pathways are transcription-dependent, in that apoptosis requires the synthesis of new proteins after stimulation by, for instance, withdrawal of growth factors. Staurosporine, a non-specific kinase inhibitor, in contrast, stimulates a transcription-independent pathway. Transcription dependent and independent pathways appear to share downstream components, including the ICE family of proteases (caspases). See Rubin, British Med. Bulle., 53:617–631, 1997, for a review of apoptosis in neurons; More general reviews include Ashkenazi and Dixit, Science 281:1305–1308; Thornberry and Lazebnik, Science 281:1312–1316; and Adams and Cory, Science 281:1322–1326.

Apoptosis is recognized as a gene-directed event, controlled by a complex set of interacting gene products that inhibit or enhance apoptosis (Williams and Smith, Cell 74:777–779, 1993; reviewed in White, Genes Dev. 10:1–15, 1996). Extensive effort is currently underway to identify and characterize the genes involved in this process. The first protein characterized as influencing apoptosis was Bcl-2 (Cleary et al., Cell 47:19–28, 1986; Tsujimoto and Croce, Proc. Natl. Acad Sci. USA 83:5214–5218, 1986). Since its discovery, several Bcl-2-related proteins (the Bcl-2 family of proteins) have been identified as being involved in regulation of apoptosis (White, Genes Dev. 10:1–15, 1996; Yang et al., Cell 80:285–291, 1995). One such is Bcl-x, which is expressed in two different forms, long (Bcl-$x_L$) and short (Bcl-$x_S$) (Boise et al., Cell 74:597–608, 1993).

Bcl-$x_L$ and certain other members of the Bcl-2 family are, like Bcl-2 itself, powerful inhibitors of cell death (the "anti-death" Bcl-2 family members). Genetic overexpression of Bcl-2 has been shown to block apoptosis in the nervous system of transgenic mice (Chen et al., Nature 385:434–439, 1997; Henkart, Immunity 4:195–201, 1996; Lippincott-Schwartz et al., Cell 67:601–616, 1991; Hunziker et al., Cell 67:617–627, 1991; Krajewski et al., Cancer Research 53:4701–4714, 1993; Martinou et al., Neuron 13:1017–1030, 1994).

Other members of the Bcl-2 protein family, including Bcl-$x_S$, Bad and Bax, are potent enhancers of apoptosis and therefore toxic to cells ("pro-death" Bcl-2 family members). Though the mechanism of apoptosis induction by these proteins remains unknown, it has been suggested that Bad binding to Bcl-$x_L$ may promote cell death (Yang et al., Cell 80:285–291, 1995; Zha et al., J Biol. Chem 272:24101–24104, 1997) and that phosphorylation of Bad may prevent its binding to Bcl-$x_L$, thereby blocking cell death (Zha et al., J Biol. Chem. 272:24101–24104, 1997; Zha et al., Cell 87:619–628, 1996).

In addition to its involvement in neuronal and lymphoid system development and overall cell population homeostasis, apoptosis also plays a substantial role in cell death that occurs in conjunction with various disease and injury conditions. For instance, apoptosis is involved in the damage caused by neurodegenerative disorders, including Alziheimer's disease (Barinaga, Science 281:1303–1304), Huntington's disease, and spinal-muscular atrophy. There is also a substantial apoptotic component to the neuronal damage caused during stroke episodes (reviewed in Rubin, British Med. Bulle., 53(3):617–631, 1997; and Barinaga, Science 281:1302–1303), and transient ischemic neuronal injury, as in spinal cord injury. It would be of great benefit to prevent undesired apoptosis in various disease and injury situations.

Treatment with standard apoptosis inhibitory molecules, for instance peptide-type caspase inhibitors (e.g., DEVD-type), though useful for laboratory experiments where microinjection can be employed, has proven unsatisfactory for clinical work due to low membrane permeability of these inhibitors. Transfection of cells with various native proteins, including members of the Bcl-2 family of regulatory proteins, has dual disadvantages. First, transfection is usually not cell-specific, and thus may disrupt apoptotic processes non-specifically in all cells. Second, transfection tends to provide long term alterations in the apoptotic process, in that once a transgene is integrated and functional in the genome of target cells, it may be difficult to turn off. Especially in instances of stroke episodes or transient ischemic neuronal injury, it would be more advantageous to be able to apply apoptosis regulation for short periods of time. Therefore, there is still a strong need to develop pharmaceutical agents that overcome these disadvantages.

Cancer and other hyper-proliferative cell conditions can be viewed as inappropriate escape from appropriate cell death. As such, it would be advantageous to be able to enhance apoptosis in certain of these cells to stop unregulated or undesired growth. Various attempts have been made to selectively eliminate cancerous cells through the use of targeted immunotoxins (genetic or biochemical fusions between a toxic molecule, for instance a bacterial toxin, and a targeting domain derived, typically from an antibody molecule).

One bacterial toxin that has been employed in attempts to kill cancerous cells is diphtheria toxin (DT). Diphtheria toxin has three structurally and functionally distinct domains: (1) a cell surface receptor binding domain (DTR), (2) a translocation domain (DTT) that allows passage of the active domain across the cell membrane, and (3) the A (enzymatically active) chain that, upon delivery to a cell, ADP-ribosylates elongation factor 2 and thereby inactivates translation. Altering the receptor specificity of the diphtheria toxin has been used to generate toxins that may selectively kill cancer cells in vitro (Thorpe et al., *Nature* 271:752–755, 1978) and in man (Laske et al., *Nature Medicine* 3:1362–1368, 1997). Promising though they might have seemed, these and similar hybrid immunotoxins have proven to be substantially less effective at targeted cell death than the toxins from which they were generated. This is perhaps due to difficulties in translocation of the fusion protein into the target cell (Columbatti et al., *J. Biol. Chem.* 261:3030–3035, 1986). In addition, in vivo results have been particularly poor using such hybrid constructs (Fulton et al., *Fed. Proc.* 461:1507, 1987).

It is to biological molecules that overcome deficiencies in the prior art that the present invention is directed.

SUMMARY OF THE DISCLOSURE

Disclosed herein are apoptosis-modifying fusion proteins constructed by fusing a protein, or an apoptosis-modifying fragment or variant thereof, from the Bcl-2 protein family with a cell-binding, targeting domain such as one derived from a bacterial toxin. Using this approach, apoptosis-modifying fusion proteins can be delivered effectively throughout the body and targeted to select tissues and cells. In certain embodiments, fusing various cell-binding domains to Bcl-2 family proteins (such as Bcl-$x_L$ or Bad) allows targeting to specific subsets of cells in vivo, permitting treatment and/or prevention of the cell-death related consequences of various diseases and injuries. The delivery of other Bcl-2 homologues to the cell permits regulation of cell viability either positively (using anti-death Bcl-2 family members), or negatively (using pro-death members of the Bcl-2 family).

The apoptosis-modifying fusion proteins disclosed herein have specifiable cell-targeting and apoptosis-modifying activities. Thus, they may be used clinically to treat various disease and injury conditions, through inhibition or enhancement of an apoptotic cellular response. For instance, apoptosis-inhibiting fusion proteins are beneficial to minimize or prevent apoptotic damage that can be caused by neurodegenerative disorders (e.g., Alzheimer's disease, Huntington's disease, spinal-muscular atrophy), stroke episodes, and transient ischemic neuronal injury (e.g., spinal cord injury). The apoptosis-enhancing fusion proteins n can be used to inhibit cell growth, for instance uncontrolled cellular proliferation.

Accordingly, a first embodiment is a functional apoptosis-modifying fusion protein capable of binding a target cell, having a first domain capable of modifying apoptosis in the target cell, and a second domain capable of specifically targeting the fusion protein to the target cell. This fusion protein further integrates into or otherwise crosses a cellular membrane of the target cell upon binding to that cell.

Certain embodiments will also include a linker between these two domains. This linker will usually be at least 5 amino acids long, for example between 5 and 100 amino acids in length, and may for instance include the amino acid sequence shown in SEQ ID NO: 6. Appropriate linkers may be 6, 7, or 8 amino acids in length, and so forth, including linkers of about 10, 20, 30, 40 or 50 amino acids long.

The apoptosis modifying fusion proteins may also include a third domain from one of the two original proteins, or from a third protein. This third domain may improve the fusion protein's ability to be integrated into or otherwise cross a cellular membrane of the target cell. An example of such a third domain is the translocation region (domain or subdomain) of diphtheria toxin.

Target cells for the fusion proteins disclosed herein include, but are not limited to, neurons, lymphocytes, stem cells, epithelial cells, cancer cells, neoplasm cells, and others, including other hyper-proliferative cells. The target cell chosen will depend on what disease or injury condition the fusion protein is intended to treat.

Receptor-binding domains may be derived from various cell-type specific binding proteins, including for instance bacterial toxins (e.g., diphtheria toxin or anthrax toxin), growth factors (e.g., epidermal growth factor), monoclonal antibodies, or single-chain antibodies derived from antibody genes. Further, variants or fragments of such proteins may also be used, where these fragments or variants maintain the ability to target the fusion protein to the appropriate target cell.

Further specific embodiments employ essentially the entire Bcl-$x_L$ protein as the apoptosis-modifying domain of the fusion protein, or variants or fragments thereof that maintain the ability to inhibit apoptosis in a target cell to which the protein is exposed. Examples of such proteins are fusion proteins made of the Bcl-$x_L$ protein, functionally linked to the diphtheria toxin receptor binding domain through a peptide linker of about six amino acids. One such protein is Bcl-$x_L$-DTR, which consists of Bcl-$x_L$ and DTR, without the translocation domain of diphtheria toxin. The nucleotide sequence of this fusion protein is shown in SEQ ID NO: 1, and the corresponding amino acid sequence in SEQ ID NOs: 1 and 2.

Another such example is LF$_n$-Bcl-$x_L$, which includes the amino terminal portion (residues 1–255) of mature anthrax lethal factor (LF), coupled to residues 1–209 of Bcl-$x_L$. The nucleotide sequence of this fusion protein is shown in SEQ ID NO: 7, and the corresponding amino acid sequence in SEQ ID NOs: 7 and 8.

Also encompassed are fusion proteins wherein the apoptosis-modifying domain is an apoptosis-enhancing domain. Such domains include the various pro-death members of the Bcl-2 family of proteins, for instance Bad, and variants or fragments thereof that enhance apoptosis in a target cell. A specific appropriate variant of the Bad protein has an amino acid other than serine at amino acid position 112 and/or position 136, to provide constitutively reduced phosphorylation.

Thus, one specific embodiment is a functional apoptosis-enhancing fusion protein capable of binding a target cell, comprising the Bad protein and the diphtheria toxin translocation and receptor binding domains, functionally linked to each other. The Bad protein of this embodiment can also contain a mutation(s) at position 112 and/or 136 to change the serine residue to some other amino acid, to reduce phosphorylation of the protein. One such protein is Bad-DTTR; the nucleotide sequence of this protein is shown in SEQ ID NO: 3, and the corresponding amino acid sequence in SEQ ID NOs: 3 and 4.

Also disclosed herein are nucleic acid molecules encoding apoptosis-modifying fusion proteins, for instance the nucleic acid sequences in SEQ ID NOs: 1, 3, and 7, and nucleic acid sequences having at least 90% sequence identity to these sequences, for instance those encoding for proteins containing one or more conservative amino acid substitutions. Other nucleic acid sequences may have 95% or 98% sequence identity with SEQ ID NO: 1, 3, or 7. Also encompassed are recombinant nucleic acid molecules in which such a nucleic acid sequence is operably linked to a promoter, vectors containing such a molecule, and transgenic cells comprising such a molecule.

Methods also are provided for producing functional recombinant apoptosis-modifying fusion proteins capable of binding to a target cell, integrating into or otherwise translocating across the cell membrane, and modifying an apoptotic response of the target cell. Such a protein can be produced in a prokaryotic or eukaryotic cell, for instance by transforming or transfecting such a cell with a recombinant nucleic acid molecule comprising a sequence which encodes a disclosed bispecific fusion protein. Appropriate eukaryotic cells include yeast, algae, plant or animal cells. Such transformed cells can then be cultured under conditions that cause production of the fusion protein, which is then recovered through protein purification means. The protein can include a molecular tag, such as a six histidine (hexa-his) tag, to facilitate its recovery.

Protein analogs, derivatives, or mimetics of the disclosed proteins, which retain the ability to target to appropriate target cells and modify apoptosis in those cells, are also encompassed in embodiments.

Compositions containing these apoptosis modifying fusion proteins, and analogs, derivatives, or mimetics of these proteins, are further aspects of this disclosure. Such compositions may further contain a pharmaceutically acceptable carrier, various other medical or therapeutic agents, and/or additional apoptosis modifying substances.

Methods for modifying apoptosis in a target cell are also encompassed, wherein a sufficient amount of a fusion protein of the current disclosure to modify apoptosis in the target cell is contacted with a target cell. Modification of apoptosis can be by either inhibition or enhancement of an apoptotic response of the target cell. The fusion protein can be administered to the target cell in the form of a pharmaceutical composition, and can further be administered with various medical or therapeutic agents, and/or additional apoptosis modifying substances. Such agents may include, for instance, chemotherapeutic, anti-inflammatory, anti-viral, and antibiotic agents.

Bcl-$x_L$-DTR, LF$_n$-Bcl-$x_L$, or related fusion proteins can be used to inhibit apoptosis in a target cell by contacting the target cell with an amount of this protein sufficient to inhibit apoptosis. Alternatively, Bad-DTTR or related fusion proteins can be used to enhance apoptosis in a target cell by contacting the target cell with an amount of this protein sufficient to enhance apoptosis.

A specific aspect disclosed herein is the method of reducing apoptosis in a subject after transient ischemic neuronal injury, for instance a spinal cord injury, comprising administering to the subject a therapeutically effective amount of an apoptosis-inhibiting protein according to this disclosure. Examples of such fusion proteins include Bcl-$x_L$-DTR and LF$_n$-Bcl-$x_L$. These proteins can be administered in the form of a pharmaceutical composition, and can be co-administered with various medical or therapeutic agents, and/or additional apoptosis modifying substances.

The foregoing and other features and advantages of the invention will become more apparent from the following detailed description of several embodiments, which proceeds with reference to the accompanying figures and tables.

BRIEF DESCRIPTION OF THE FIGURES

FIG. 1A is a schematic representation of construction of Bcl-$x_L$-DTR. FIG. 1B is a Western blot of the lysates of HeLa cells transiently transfected with Bcl-$x_L$ (lane b) and Bcl-$x_L$-DTR (lane c). Lane a contains untransfected cells as a control. A small amount of endogencous Bcl-$x_L$ is present in lanes a and c. FIG 1C is a graph that shows transient transfection of Bcl-$x_L$ (○) and Bcl-$x_L$-DTR (◇) genes into HeLa cells inhibits apoptotic cell death induced by the addition of STS. Apoptosis in control cells transfected with the vector (pcDNA3) vector is shown for comparison (□).

FIG. 3B is a SDS-PAGE gel that shows that Bcl-$x_L$-DTR prevents PARP cleavage. Lane a contains control HeLa cells not incubated with STS (uninduced cells); Lane b, HeLa cells treated with STS plus 1 μμM Bcl-$x_L$-DTR protein; Lane c, HeLa cells treated with STS plus 1.48 μM Bcl-$x_L$-DTR protein; and Lane d, HeLa cells treated with STS and no fusion protein.

FIG. 4A is a graph showing that the addition of Bcl-$x_L$-DTR prior to irradiation of Jurkat cells reduces apoptotic death in response toy-radiation. Control cells were not irradiated and not treated with Bcl-$x_L$-DTR. FIG. 4B is a graph that shows that, in Jurkat cells, Bcl-$x_L$-DTR had little inhibitory effect on apoptosis induced by anti-Fas antibody. Control cells were treated with PBS and no anti-Fas antibody.

FIG. 7A is a graph quantifying cell death after treatment of U251 MG cells with various combinations of STS and Bad-DTTR. Apoptosis is most enhanced when cells are treated with 0.1 μM STS plus 0.65 μM Bad-DTTR, and cells begin to die about 12 hours after treatment. In the experiment depicted in FIG. 7B, the use of 1 μM STS in combination with various concentrations of Bad-DTTR cause an earlier onset of apoptosis in U251 MG cells. Key: □=PBS; ◇=0.1 μM STS; ○=0.65 μM Bad-DTTR; ∆=0.065 μM Bad-DTTR; ☞=0.1 μM STS+0.65 μM Bad-DTTR; ⊖=0.1 μM STS+0.065 μM Bad-DTTR.

FIG. 8 is a schematic diagram of the chimera $LF_n$-Bcl-$x_L$. The fusion gene, $LF_n$-Bcl-$x_L$, was inserted into the vector, pET15b, yielding a histidine tag sequence at the N terminus of the $LF_n$-Bcl-$x_L$ gene.

FIG. 9 is a graph showing the time course of apoptosis induced by STS in J774 cells, with or without $LF_n$-Bcl-$x_L$ protein. J774 cells at $3 \times 10^4/cm^2$ were treated with 0.1 μM staurosporine alone, 0.1 μM staurosporine along with $LF_n$-Bcl-$x_L$ (28 μg/ml) plus PA (33 μ/ml), or with PBS alone. The apoptotic and living cells were stained with Hoechst 33342 and counted at the indicated times, and the data were calculated as reported (Liu et al., *Proc. Natl. Acad. Sci. USA* 96: 9563–9567, 1999).

SEQUENCE LISTING

Figure 1A:
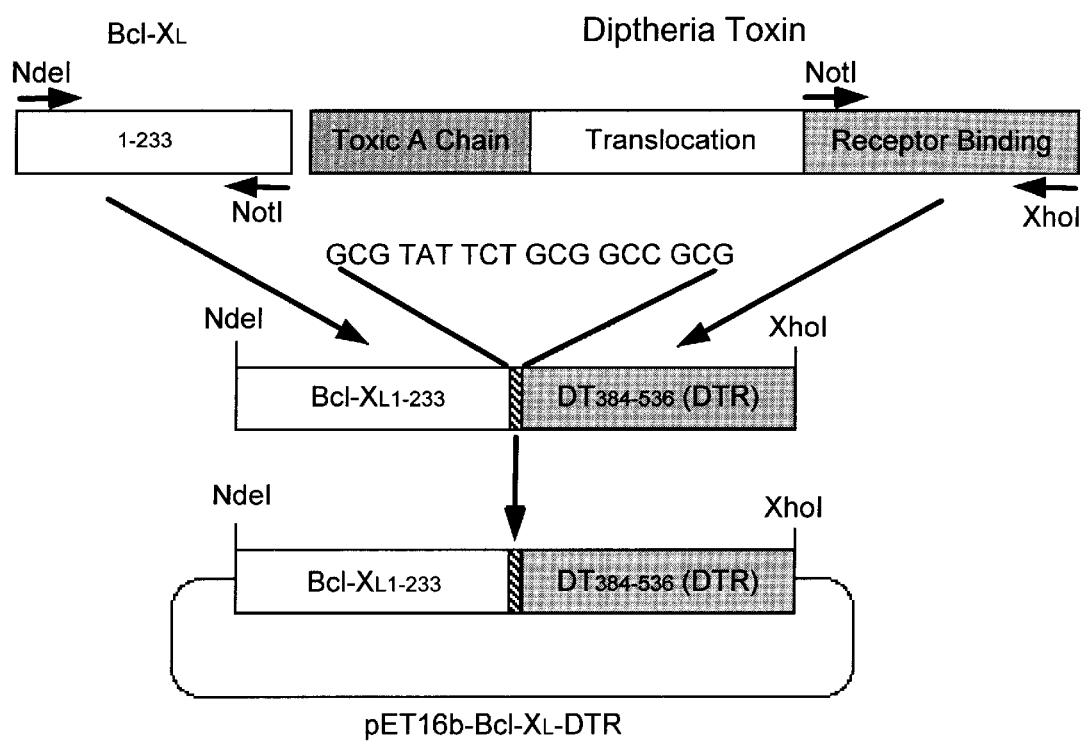
FIGS. 1A–C shows the construction, production and bioactivity of Bcl-$x_L$-DTR and Bcl-$x_L$ transfected into HeLa cells.

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NO: 1 shows the DNA coding sequence and corresponding amino acid sequence of Bcl-$x_L$-DTR.

SEQ ID NO: 2 shows the amino acid sequence of Bcl-$x_L$-DTR.

SEQ ID NO: 3 shows the DNA coding sequence and corresponding amino acid sequence of Bad-DTTR.

SEQ ID NO: 4 shows the amino acid sequence of Bad-DTTR. SEQ ID NO: 5 shows the nucleotide sequence of the linker used to link Bcl-$x_L$ to DTR in the fusion construct Bcl-$x_L$-DTR.

SEQ ID NO: 6 shows the amino acid sequence of the linker used to link Bcl-$x_L$ to DTR to form Bcl-$x_L$-DTR.

SEQ ID NO: 7 shows the DNA coding sequence and corresponding amino acid sequence of $LF_n$-Bcl-$x_L$.

SEQ ID NO: 8 shows the amino acid sequence of $LF_n$-Bcl-$x_L$.

DETAILED DESCRIPTION OF THE INVENTION

I. Abbreviations and Definitions

A. Abbreviations

DT: diphtheria toxin

DTR: diphtheria toxin receptor binding domain

DTT: diphtheria toxin translocation domain

DTTR: diphtheria toxin translocation and receptor binding domains

*E. coli*: *Escherichia coli*

EF: anthrax edema factor

LF: anthrax lethal factor $LF_n$: first 255 residues of anthrax lethal factor moi: multiplicity of infection PA: anthrax protective antigen PCR: polymerase chain reaction RE: restriction endonuclease SDS-PAGE: sodium dodecyl sulfate-polyacrylamide gel electrophoresis STS: staurosporine TdT: terminal deoxyribonucleotidyl transferase TUNEL: TdT-dependent dUTP-biotin nick end labeling B. Definitions Unless otherwise noted, technical terms are used according to conventional usage. Definitions of common terms in molecular biology may be found in Lewin, *Genes V* published by Oxford University Press, 1994 (ISBN 0-19-854287-9); Kendrew et al., (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). The nomenclature for DNA bases and the three-letter code for amino acid residues, as set forth at 37 CFR §1.822, are used herein.

In order to facilitate review of the various embodiments of the invention, the following definitions of terms are provided. These definitions are not intended to limit such terms to a scope narrower than would be known to a person of ordinary skill in the field.

Animal: Living multi-cellular vertebrate organisms, a category that includes, for example, mammals and birds. The term mammal includes both human and non-human mammals. Similarly, the term "subject" includes both human and veterinary subjects.

Apoptosis-modifying ability: A protein has apoptosis-modifying ability if it is capable of modifying apoptosis in a cell. This ability is usually measurable, either in vivo or in vitro, using any one of myriad apoptosis assays. The art is replete with methods for measuring apoptosis. Appropriate techniques include dye exclusion (e.g. Hoechst dye No. 33342), assaying for caspase activity, and TUNEL-staining. The specific ability of a fusion protein to modify the apoptotic response of a cell to various apoptosis-inducing stimuli can be determined by running standard apoptosis assays in the absence of or presence of various concentrations of the fusion proteins. The results of the assay are then compared, and can be reported for instance by presenting the percentage of apoptosis that occurs in the presence of the fusion protein.

The invention also includes analogs, derivatives or mimetics of the disclosed fusion proteins, and which have apoptosis-modifying ability. Such molecules can be screened for apoptosis-modifying ability by assaying a protein similar to the disclosed fusion protein, in that it has one or more conservative amino acid substitutions or short in-frame deletions or insertions, or analogs, derivatives or mimetics thereof, and determining whether the similar protein, analog, derivative or mimetic provides modification of apoptosis in a desired target cell. The apoptosis-modifying ability and target cell binding affinity of these derivative compounds can be measured by any known means, including those discussed in this application.

Apoptosis-modifying fusion protein: Proteins that have at least two domains fused together, at least one domain comprising a cell binding region capable of targeting the fusion protein to a target cell (the targeting or cell-binding domain), and at least one domain capable of modifying apoptosis in the target cell (the apoptosis-modifying domain). The apoptosis-modifying fusion proteins of the current invention are further characterized by their ability to integrate into or otherwise cross a cellular membrane of the target cell when delivered extracellularly. An apoptosis-modifying fusion protein is considered functional if it targets to the correct target cell, and modifies an apoptotic response of that cell.

In general, the two domains of the disclosed fusions are genetically fused together, in that nucleic acid molecules that encode each protein domain are functionally linked together, for instance directly or through the use of a linker oligonucleotide, thereby producing a single fusion-encoding nucleic acid molecule. The translated product of such a fusion-encoding nucleic acid molecule is the apoptosis-modifying fusion protein.

Apoptosis-modifying fusion proteins can be labeled according to how they influence apoptosis in the target cell. For instance, an apoptosis-modifying fusion protein according to the current invention that inhibits apoptosis in the target cell can be referred to as an apoptosis-inhibiting fusion protein (e.g., Bcl-$x_L$-DTR and LF$_n$-Bcl-$x_L$). Likewise, if the fusion protein enhances apoptosis in the target cell, it can be referred to as an apoptosis-enhancing fusion protein (e.g., Bad-DTR). Specific apoptosis-modifying fusion proteins are usually named for the proteins from which domains are taken to form the fusion, or from the domains actually used. For instance, "Bcl-$x_L$-DTR" (SEQ ID NOs: 1 and 2) consists of the entire Bcl-$x_L$ protein fused in frame to the receptor-binding domain of diphtheria toxin (DTR) via a short linker.

A Bcl-2 protein: A Bcl-2 protein is a protein from the Bcl-2 family of proteins and includes those proteins related to Bcl-2 by sequence homology, which affect apoptosis. By way of example, the family includes Bcl-2, Bcl-x (both the long and short forms), Bax, and Bad. Additional members of the Bcl-2 family of proteins are known (Adams and Cory, *Science* 281:1322–1326, 1998).

Molecules that are derived from proteins of the Bcl-2 family include fragments of such proteins (e.g., fragments of Bcl-$x_L$ or Bad), generated either by chemical (e.g., enzymatic) digestion or genetic engineering means. Such fragments may comprise nearly all of the native protein, with one or a few amino acids being genetically or chemically removed from the amino or carboxy terminal end of the protein, or genetically removed from an internal region of the sequence.

Derived molecules, or derived from: The term "X-derived molecules" or "derived from X," where X is a protein also encompasses analogs (non-protein organic molecules), derivatives (chemically functionalized molecules obtained starting with the disclosed protein sequences) or mimetics (three-dimensionally similar chemicals) of the native protein structure, as well as proteins sequence variants or genetic alleles, that maintain biological functionality. Where the derived molecule is used as the targeting domain of an apoptosis-modifying fusion protein, the biological functionality maintained is the ability to target to fusion protein to the desired target cell. Likewise, where the derived molecule is used as the apoptosis-modifying domain of the fusion, the functionality maintained is the ability to affect apoptosis in the target cell. Each of these functionalities can be measured in various ways, including specific protein binding and apoptosis assays, respectively.

Injectable composition: A pharmaceutically acceptable fluid composition comprising at least one active ingredient, e.g., an apoptosis-modifying fusion protein. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this invention are conventional; appropriate formulations are well known in the art.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linker: A peptide, usually between two and 150 amino acid residues in length, which serves to join two protein domains in a multi-domain fusion protein. Peptide linkers are generally encoded for by a corresponding oligonucleotide linker. This can be genetically fused, in frame, between the nucleotides that encode the domains of a fusion protein.

Oligonucleotide: A linear polynucleotide sequence of between six and 300 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this invention are conventional. Martin, *Remington's Pharmiaceutical Sciences*, published by Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Purified: The term purified does not require absolute purity, rather, it is intended as a relative term. Thus, for example, a purified fusion protein preparation is one in which the fusion protein is more enriched than the protein is in its generative environment, for instance within a cell or in a biochemical reaction chamber. Preferably, a preparation of fusion protein is purified such that the fusion protein represents at least 50% of the total protein content of the preparation. More purified preparations will have fusion protein that represents at least 60%, 70%, 80% or 90% of the total protein content.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the apoptosis-modifying fusion protein will possess a relatively high degree of sequence identity when aligned using standard methods. For instance, encoding sequences encompassed in the current invention include those that share about 90% sequence identity with SEQ ID NO: 1 and NO: 3.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *PNAS. USA* 85:2444, 1988; Higgins and Sharp, *Gene*, 73:237–244, 1988; Higgins and Sharp, *CABIOS* 5:151–153, 1989; Corpet et al., *Nuc. Acids Res.* 16:10881–90, 1988; Huang et al., *Comp. Appls Biosci.* 8:155–65, 1992; and Pearson et al., *Meth. Mol. Biol.* 24:307–31, 1994. Altschul et al., *Nature Genet.* 6:119–29, 1994, presents a detailed consideration of sequence alignment methods and homology calculations.

The alignment tools ALIGN (Myers and Miller, *CABIOS* 4:11–17, 1989) or LFASTA (Pearson and Lipman, *PNAS. USA* 85:2444, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA web-site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 90%, at least 92%, at least 94%, at least 95%, at least 97%, at least 98%, or at least 99% sequence identity.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al., In *Molecular Cloning: A Laboratory Manual*, Cold Spring Harbor, N.Y., 1989, and Tijssen, *Laboratory Techniques in Biochemistry and Molecular Biology* Part I, Ch. 2, Elsevier, N.Y., 1993. Nucleic acid molecules that hybridize to the disclosed apoptosis-modifying fusion protein sequences under stringent conditions will typically hybridize to a probe (based on the entire fusion protein encoding sequence, an entire domain, or other selected portions of the encoding sequence) under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that encode substantially the same protein.

Specific binding agent: An agent that binds substantially only to a defined target. Thus a Bcl-$x_L$-DTR-specific binding agent binds substantially only the Bcl-$x_L$-DTR protein in a specific preparation. As used herein, the term "Bcl-$x_L$-DTR-specific binding agent" includes Bcl-$x_L$-DTR antibodies and other agents that bind substantially only to a Bcl-$x_L$-DTR protein in that preparation.

Anti-Bcl-$x_L$-DTR antibodies may be produced using standard procedures described in a number of texts, including Harlow and Lane (*Using Antibodies, A Laboratory Manual*, CSHL, New York, 1999, ISBN 0-87969-544-7). The determination that a particular agent binds substantially only to Bcl-$x_L$-DTR protein may readily be made by using or adapting routine procedures. One suitable in vitro assay makes use of the Western blotting procedure (described in many standard texts, including Harlow and Lane, 1999). Western blotting may be used to determine that a given protein binding agent, such as an anti-Bcl-$x_L$-DTR monoclonal antibody, binds substantially only to the Bcl-$x_L$-DTR protein.

Alternately, because the disclosed apoptosis-modifying proteins are fusion proteins, they can be detected using antibodies to one or the protein domains used in their construction. For instance, fusions containing Bcl-$x_L$ can be detected using the monoclonal antibody 2H12 (Hsu and Youle, *J. Biol. Chem.* 272:13829–13834, 1997; now available from Neo Markers, Union City, Calif., clone #2H121-3) or other professionally available antibody preparations, for instance, polyclonal anti-Bcl-$x_L$/$x_S$ #06-851 from Upstate Biotechnology, Lake Placid, N.Y.; polyclonal rabbit anti-Bcl-$x_L$ #65189E from PharMingen, San Diego, Calif.; and rabbit polyclonal (#B22630-050/B22630-150) or mouse monoclonal (B61220-050/B61220-150) anti-Bcl-$x_L$ from Transduction Laboratories, Lexington, Ky.). Antibodies that recognize diphtheria toxin are, for instance, available from the Centers for Disease Control, Atlanta, Ga.

Shorter fragments of antibodies can also serve as specific binding agents. For instance, FAbs, Fvs, and single-chain Fvs (SCFvs) that bind to Bcl-$x_L$-DTR would be Bcl-$x_L$-DTR-specific binding agents.

Target cell binding affinity: The physical interaction between a target cell and an apoptosis-modifying fusion protein as disclosed in this invention can be examined by various methods. Alternatively, the ability of fusion protein to compete for binding to its target cell with either native targeting domain or antibody that recognizes the targeting domain binding site on the target cell can be measured. This allows the calculation of relative binding affinities through standard techniques.

Therapeutically effective amount of an apoptosis-modifying fusion protein: A quantity of apoptosis-modifying fusion protein sufficient to achieve a desired effect in a subject being treated. For instance, this can be the amount necessary to measurably inhibit or enhance apoptosis in a target cell.

An effective amount of apoptosis-modifying fusion protein may be administered in a single dose, or in several doses, for example daily, during a course of treatment. However, the effective amount of fusion protein will be dependent on the fusion protein applied, the subject being treated, the severity and type of the affliction, and the manner of administration of the fusion protein. For example, a therapeutically effective amount of fusion protein can vary from about 0.01 mg/kg body weight to about 1 g/kg body weight.

The fusion proteins disclosed in the present invention have equal application in medical and veterinary settings. Therefore, the general term "subject being treated" is understood to include all animals (e.g., humans, apes, dogs, cats, horses, and cows), and particularly mammals, that are or may suffer from a chronic or acute condition or injury that causes apoptosis, or a lack thereof, susceptible to modification using molecules of the current invention.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic cell: A transgenic cell is one that has been transformed with a recombinant nucleic acid molecule.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

II. Construction, Expression, and Purification of Apoptosis-Modifying Fusion Proteins A. Selection of Component Domains.

This invention provides generally an apoptosis-modifying fusion protein that binds to a target cell, translocates across or otherwise integrates into the membrane(s) of the target cell, and modifies an apoptotic response of the target cell. As such, any target cell in which it is desirous to modify (either inhibit or enhance) apoptosis is an appropriate target for a bispecific fusion protein. The choice of appropriate protein binding domain for incorporation into the disclosed apoptosis-modifying fusion protein will be dictated by the target cell or cell population chosen. Examples of targeting domains include, for instance, nontoxic cell binding domains or components of bacterial toxins (such as diphtheria toxin or anthrax toxin), growth factors (such as epidermal growth factor), monoclonal antibodies, cytokines, and so forth, as well as targeting competent variants and fragments thereof.

The choice of appropriate Bcl-2 family member-derived apoptosis-modifying domain will depend on the manner in which the target cell's response to apoptosis is to be modified. Where apoptosis is to be inhibited by the resultant fusion protein, anti-death members of the Bcl-2 protein family are appropriate sources for apoptosis-modifying domains. One such fusion protein is Bcl-$x_L$-DTR, which employs the long form of Bcl-x, Bcl-$x_L$, as the apoptosis-modifying domain. Alternately, where enhancement of apoptosis is desired, pro-death members of the Bcl-2 family of proteins will be appropriate. For instance, Bad-DTTR employs the pro-death protein Bad as its apoptosis-modifying domain.

Translocation of the apoptosis-modifying fusion protein into the target cell is important. A translocation domain may be included in the fusion protein as a separate, third domain. This could be supplied from a third protein, unrelated to the cell-binding and apoptosis-modifying domains, or be a translocation domain of one of these proteins (e.g., the diphtheria toxin translocation (DTT) domain used in Bad-DTTR). The DTT domain contains several hydrophobic and amphipathic alpha helices and, after insertion into cell membranes, creates voltage dependent ion channels (Kagan et al., *Proc Natl Acad Sci USA* 78:4950–4954, 1981; Donovan et al., *Proc Natl Acad Sci USA* 78: 172–176, 1981).

Alternately, the translocation function can be provided through the use of a cell-binding domain or apoptosis-modifying domain that confers the additional functionality of membrane translocation or integration. This is true in Bcl-$x_L$-DTR, wherein Bcl-$x_L$ provides both the apoptosis-modifying ability and translocation into the cell.

B. Assembly

The construction of fusion proteins from domains of known proteins is well known. In general, a nucleic acid molecule that encodes the desired protein domains are joined using standard genetic engineering techniques to create a single, operably linked fusion oligonucleotide. Appropriate molecular biological techniques may be found in Sambrook et al, In *Molecular Cloning: A Laboratory Manual*, Cold Spring Harbor, N.Y., 1989. Specific examples of genetically engineered multi-domain proteins, including those joined by various linkers, can be found in the following patent documents:

U.S. Pat. No. 5,834,209 to Korsmeyer;
U.S. Pat. No. 5,821,082 to Chinnadurai;

U.S. Pat. No. 5,696,237 to FitzGerald et al.;
U.S. Pat. No. 5,668,255 to Murphy;
U.S. Pat. No. 5,587,455 to Berger et al.;
WO 98/17682 to Korsmeyer; and
WO 98/12328 to Home et al.

It will usually be convenient to generate various control molecules for comparison to an apoptosis-modifying fusion protein, in order to measure the specificity of the apoptosis modification provided by each fusion protein. Appropriate control molecules may include one or more of the native proteins used in construction of the fusion, or fragments or mutants thereof C. Expression One skilled in the art will understand that there are myriad ways to express a recombinant protein such that it can subsequently be purified. In general, an expression vector carrying the nucleic acid sequence that encodes the desired protein will be transformed into a microorganism for expression. Such microorganisms can be prokaryotic (bacteria) or eukaryotic (e.g., yeast). One appropriate species of bacteria is Escherichia coli (*E. coli*), which has been used extensively as a laboratory experimental expression system. A eukaryotic expression system will be preferred where the protein of interest requires eukaryote-specific post-translational modifications such as glycosylation. Also, protein can be expressed using a viral (e.g., vaccinia) based expression system.

Protein can also be expressed in animal cell tissue culture, and such a system will be appropriate where animal-specific protein modifications are desirable or required in the recombinant protein.

The expression vector can include a sequence encoding a synthesis targeting peptide, positioned in such a way as to be fused to the coding sequence of the apoptosis-modifying fusion protein. This allows the apoptosis-modifying fusion protein to be targeted to specific sub-cellular or extracellular locations. Various appropriate prokaryotic and eukaryotic targeting peptides, and nucleic acid molecules encoding such, are well known to one of ordinary skill in the art. In a prokaryotic expression system, a signal sequence can be used to secrete the newly synthesized protein. In a eukaryotic expression system, the targeting peptide would specify targeting of the hybrid protein to one or more specific sub-cellular compartments, or to be secreted from the cell, depending on which peptide is chosen. Through the use of a eukaryotic secretion signal sequence, the apoptosis-modifying fusion protein can be expressed in a transgenic animal (for instance a cow, pig, or sheep) in such a manner that the protein is secreted into the milk of the animal.

Vectors suitable for stable transformation of culturable cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site. For production of large amounts of recombinant proteins, an inducible promoter is preferred. This permits selective production of the recombinant protein, and allows both higher levels of production than constitutive promoters, and enables the production of recombinant proteins that may be toxic to the expressing cell if expressed constitutively.

In addition to these general guidelines, protein expression/purification kits are produced commercially. See, for instance, the QIAexpress™ expression system from QIAGEN (Chatsworth, Calif.) and various expression systems provided by INVITROGEN (Carlsbad, Calif.). Depending on the details provided by the manufactures, such kits can be used for production and purification of the disclosed apoptosis-modifying fusion proteins.

D. Purification

One skilled in the art will understand that there are myriad ways to purify recombinant polypeptides, and such typical methods of protein purification may be used to purify the disclosed apoptosis-modifying fusion proteins. Such methods include, for instance, protein chromatographic methods including ion exchange, gel filtration, HPLC, monoclonal antibody affinity chromatography and isolation of insoluble protein inclusion bodies after over production. In addition, purification affinity-tags, for instance a six-histidine sequence, may be recombinantly fused to the protein and used to facilitate polypeptide purification. A specific proteolytic site, for instance a thrombin-specific digestion site, can be engineered into the protein between the tag and the fusion itself to facilitate removal of the tag after purification.

Commercially produced protein expression/purification kits provide tailored protocols for the purification of proteins made using each system. See, for instance, the QIAexpress™ expression system from QIAGEN (Chatsworth, Calif.) and various expression systems provided by INVITROGEN (Carlsbad, Calif.). Where a commercial kit is employed to produce a bispecific fusion protein, the manufacturer's purification protocol is a preferred protocol for purification of that protein. For instance, proteins expressed with an amino-terminal hexa-histidine tag can be purified by binding to nickel-nitrilotriacetic acid (Ni-NTA) metal affinity chromatography matrix (The *QIAexpressionist*, QIAGEN, 1997).

Alternately, the binding specificities of the cell-binding/targeting domain of the disclosed apoptosis-modifying protein may be exploited to facilitate specific purification of the proteins. A preferred method of performing such specific purification would be column chromatography using column resin to which the target cell surface receptor, or an appropriate epitope or fragment or domain of the target molecule, has been attached.

If the apoptosis-modifying fusion protein is produced in a secreted form, e.g. secreted into the milk of a transgenic animal, purification will be from the secreted fluid. Alternately, purification may be unnecessary if it is appropriate to apply the fusion protein directly to the subject in the secreted fluid (e.g. milk).

III. Variation of a Bispecific Fusion Protein

A. Sequence Variants

The binding and apoptosis-modifying characteristics of the apoptosis-modifying fusion proteins disclosed herein lies not in the precise amino acid sequence, but rather in the three-dimensional structure inherent in the amino acid sequences encoded by the DNA sequences. It is possible to recreate the functional characteristics of any of these proteins or protein domains of this invention by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a functional apoptosis-modifying fusion protein.

Variant apoptosis-modifying fusion proteins include proteins that differ in amino acid sequence from the disclosed sequence but that share structurally significant sequence homology with any of the provided proteins. Variation can occur in any single domain of the fusion protein (e.g., the binding or apoptosis-modifying domain, or, where appropriate, the linker). Variation can also occur in more than one of such domains in any particular variant protein. Such variants may be produced by manipulating the nucleotide sequence of, for instance, a Bcl-$x_L$-encoding sequence, using standard procedures, such as site-directed mutagenesis or PCR. The simplest modifications involve the substitution of one or more amino acids for amino acids having similar biochemical properties. These so-called conservative substitutions are likely to have minimal impact on the activity of the resultant protein, especially when made outside of the binding site or active site of the respective domain. The regions or sub-domains of DTR that are essential to targeted cell binding are known in the art (see, Choe et al., Nature 357:216–222, 1992; Parker and Pattus, TIBS 18:391–395, 1993). Regions or sub-domains of Bcl-2 proteins responsible for apoptosis modification are under intense study; much of this work is reviewed in Adams and Cory, *Science* 281:1322–1326.

Table 1 shows amino acids that may be substituted for an original amino acid in a protein, and which are regarded as conservative substitutions.

TABLE 1

| Original Residue | Conservative Substitutions |
| --- | --- |
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

More substantial changes in protein structure may be obtained by selecting amino acid substitutions that are less conservative than those listed in Table 1. Such changes include changing residues that differ more significantly in their effect on maintaining polypeptide backbone structure (e.g., sheet or helical conformation) near the substitution, charge or hydrophobicity of the molecule at the target site, or bulk of a specific side chain. The following substitutions are generally expected to produce the greatest changes in protein properties: (a) a hydrophilic residue (e.g., seryl or threonyl) is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histadyl) is substituted for (or by) an electronegative residue (e.g., glutamyl or aspartyl); or (d) a residue having a bulky side chain (e.g., phenylalanine) is substituted for (or by) one lacking a side chain (e.g., glycine).

Variant binding domain, apoptosis-modifying domain, or fusion protein-encoding sequences may be produced by standard DNA mutagenesis techniques, for example, M13 primer mutagenesis. Details of these techniques are provided in Sambrook et al., In *Molecular Cloning: A Laboratory Manual*, Cold Spring Harbor, N.Y., 1989, Ch. 15. By the use of such techniques, variants may be created which differ in minor ways from the apoptosis-modifying fusion protein-encoding sequences disclosed. DNA molecules and nucleotide sequences which are derivatives of those specifically disclosed herein and that differ from those disclosed by the deletion, addition, or substitution of nucleotides while still encoding a protein that binds to a target cell, translocates or otherwise integrates into the target cell membrane(s), and thereby modifies an apoptotic response in the target cell, are comprehended by this invention. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed fusion sequences. For example, the 57th amino acid residue of the Bcl-$x_L$-DTR protein is alanine. The nucleotide codon triplet GCC encodes this alanine residue. Because of the degeneracy of the genetic code, three other nucleotide codon triplets—(GCG, GCT and GCA)—also code for alanine. Thus, the nucleotide sequence of the disclosed Bcl-$x_L$-DTR encoding sequence could be changed at this position to any of these three alternative codons without affecting the amino acid composition or characteristics of the encoded protein. Based upon the degeneracy of the genetic code, variant DNA molecules may be derived from the cDNA and gene sequences disclosed herein using standard DNA mutagenesis techniques as described above, or by synthesis of DNA sequences. Thus, this invention also encompasses nucleic acid sequences which encode an apoptosis-modifying fusion protein, but which vary from the disclosed nucleic acid sequences by virtue of the degeneracy of the genetic code. Apoptosis assays, including those discussed herein, can be used to determine the ability of the resultant variant protein to modify apoptosis.

B. Peptide Modifications

The present invention includes biologically active molecules that mimic the action of the apoptosis-modifying fusion proteins of the present invention, and specifically modify apoptosis in a target cell. The proteins of the invention include synthetic versions of naturally-occurring proteins described herein, as well as analogues (non-peptide organic molecules), derivatives (chemically functionalized protein molecules obtained starting with the disclosed peptide sequences) and variants (homologs) of these proteins that specifically bind to a chosen target cell and modify apoptosis in that target cell. Each protein of the invention is comprised of a sequence of amino acids, which may be either L- and/or D-amino acids, naturally occurring and otherwise.

Proteins may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide.

Hydroxyl groups of the protein side chains may be converted to $C_1$–$C_{16}$ alkoxy or to a $C_1$–$C_{16}$ ester using well-recognized techniques. Phenyl and phenolic rings of the protein side chains may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the protein side chains can be extended to homologous $C_2$–$C_4$ alkylenes. Thiols can be protected with any one of a number of well-recognized protecting groups, such as acetamide groups. Those skilled in the art will also recognize methods for introducing cyclic structures into the proteins of this invention to select and provide conformational constraints to the structure that result in enhanced stability.

Peptidomimetic and organomimetic embodiments are also within the scope of the present invention, whereby the three-dimensional arrangement of the chemical constituents of such peptido- and organomimetics mimic the three-dimensional arrangement of the protein backbone and component amino acid side chains in the apoptosis-modifying fusion protein, resulting in such peptido- and organomimetics of the proteins of this invention having measurable or enhanced neutralizing ability. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, Computer-Assisted Modeling of Drugs, in Klegerman & Groves (eds.), *Pharmaceutical Biotechnology*, Interpharm Press: Buflalo Grove, Ill., 165–174, 1993; and Munson (ed.) *Principles of Pharmacology*, Ch. 102, 1995, for descriptions of techniques used in CADD. Also included within the scope of the invention are mimetics prepared using such techniques that produce apoptosis-modifying fusion proteins.

IV. Activity of Fusion Proteins

Because the apoptosis modifying fusion proteins provided in this invention are at least bi-functional, having one domain required for cell targeting and another for modification of apoptosis in the target cell, there are at least two activities for each fusion protein. These include the affinity of the fusion protein for a specific target cell, class of target cells, tissue type, etc., (the binding ability), and the ability of the targeted fusion to effect apoptosis in the targeted cell (the apoptosis-modifying ability). Various techniques can be used to measure each of these activities.

A. Fusion Protein Affinity for Target Cells

Fusion protein affinity for the target cell, or to a specific cell surface protein, can be determined using various techniques known in the art. One common method is a competitive binding assay (Greenfield et al., *Science* 238:536–539, 1987). In a competitive binding assay, radiolabeled receptor binding protein, or a derivative or fragment thereof, is exposed to the target native cell in the presence of one or varying concentrations of cold fusion protein and other competitive proteins being assayed. The amount of bound, labeled binding protein can be measured through standard techniques to determine the relative cell-binding affinity of the fusion.

B. Apoptosis Inhibition or Enhancement

Several in vitro systems are used to study the process of apoptosis. These include growth factor deprivation in culture, treatment of cells with staurosporine (a non-specific protein kinase inhibitor), application of γ-radiation, and infection by viruses. Apoptosis as stimulated by any signal can be examined or measured in a variety of ways. Detection of morphological indicia of apoptosis (e.g., membrane blebbing, chromatin condensation and fragmentation, and formation of apoptotic bodies) can provide qualitative information. More quantitative techniques include TUNEL staining, measurement of DNA laddering, measurement of known caspase substrate degradation (e.g., PARP; Taylor et al., *J. Neurochem.* 68:1598–605, 1997) and counting dying cells, which have become susceptible to dye uptake. Many companies (e.g., Trevigen, Gaithersburg Md., and R&D Systems, Minneapolis Minn.) also supply kits useful for the measurement of apoptosis by various methods; many of these kits can be used to measure the effect of disclosed apoptosis-modifying fusion proteins on apoptosis in a variety of cell types.

By way of example, the following techniques can be used to measure the modification of apoptosis caused in a target cell after it is contacted with an apoptosis-modifying fusion protein of the present invention.

TUNEL staining: Terminal end-labeling of broken DNA fragments with labeled nucleotides; the reaction is catalyzed by terminal nucleotide transferase (TdT). Various kits are available for measurement of TUNEL staining, including the TdT in situ TUNEL-based Kit (R&D Systems, Minneapolis, Minn.).

Measurement of Caspase Activity: Another common system for measuring the amount of apoptosis occurring in an in vitro cell system is to measure the poly-ADP ribose Polymerase (PARP) cleavage after treatment of the cells with various stimulators of apoptosis. PARP is a known substrate for a caspase (CPP-32) involved in the apoptotic kinase cascade. This technique can be carried out using essentially the following protocol. HeLa cells are plated in growth media (e.g., EMEM containing 10% FBS at $2 \times 10^5$ cells/ml) and treated with one or more concentrations of an apoptosis-modifying fusion protein according to the current invention. The appropriate concentration for each fusion protein will depend on various factors, including the fusion protein in question, target cell, and apoptosis stimulator employed. Appropriate concentrations may include, for instance, about 0.5 μM to about 3 μM final. It may be beneficial to treat the target cells multiple times with the fusion protein, usually after a period of incubation ranging from one to several hours. For instance, cells can be exposed to the fusion protein a second time about fifteen hours after the original treatment. Usually the same concentration(s) of fusion protein is used in the second treatment.

Apoptosis is induced immediately the last treatment of the target cells with apoptosis modifying fusion protein. The method of application of the apoptosis stimulus, amount applied, appropriate incubation time with the inducer, etc., will be specific to the type of apoptosis induction used (e.g., staurosporine, γ-radiation, virions, caspase inhibitor, etc.). Such details are in general well known to those of ordinary skill in the art. After an appropriate incubation period, cell lysates are prepared from the treated target cells, and aliquots loaded onto SDS-PAGE for analysis. The resultant gels can be examined using any of various well-known techniques, for instance by performing a Western analysis immunoblotted with anti-PARP polyclonal antibody (Boehringer Mannheim GmbH, Germany), developed with enhanced chemiluminescence.

Known inhibitors of apoptotic pathways, for instance caspase inhibitors, can be used to compare the effectiveness of apoptosis-modifying fusion proteins of this invention. Appropriate inhibitors include viral caspase inhibitors like crmA and baculovirus p35, and peptide-type caspase inhibitors including zVAD-fink, YVAD- and DEVD-type inhibitors. See Rubin, *British Med. Bulle.*, 53:617–631, 1997.

V. Incorporation of Apoptosis-Modifying Fusion Proteins Into Pharmaceutical Compositions Pharmaceutical compositions that comprise at least one apoptosis modifying fusion protein as described herein as an active ingredient will normally be formulated with an appropriate solid or liquid carrier, depending upon the particular mode of administration chosen. The pharmaceutically acceptable carriers and excipients useful in this invention are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

One or more other medicinal and pharmaceutical agents, for instance chemotherapeutic, anti-inflammatory, anti-viral or antibiotic agents, also may be included.

The dosage form of the pharmaceutical composition will be determined by the mode of administration chosen. For instance, in addition to injectable fluids, topical and oral formulations can be employed. Topical preparations can include eye drops, ointments, sprays and the like. Oral formulations may be liquid (e.g., syrups, solutions or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that comprise apoptosis modifying fusion protein will preferably be formulated in unit dosage form, suitable for individual administration of precise dosages. One possible unit dosage contains approximately 100 μg of protein. The amount of active compound administered will be dependent on the subject being treated, the severity of the affliction, and the manner of administration, and is best left to the judgment of the prescribing clinician. Within these bounds, the formulation to be administered will contain a quantity of the active component(s) in an amount effective to achieve the desired effect in the subject being treated. Ideally, a sufficient amount of the protein is administered to achieve tissue a concentration at the site of action that is at least as great as in vitro concentrations that have been shown to be effective.

VI. Clinical Use of Apoptosis-Modifying Fusion Proteins

The targeted apoptosis-regulating activity exhibited by the disclosed fusion proteins makes these fusions useful for treating neurodegenerative diseases, transient ischemic injuries, and unregulated cell growth (as may for instance be found in tumors and various cancers The apoptosis-modifying fusion proteins of this invention may be administered to humans, or other animals on whose cells they are effective, in various manners such as topically, orally, intravenously, intramuscularly, intraperitoneally, intranasally, intradermally, intrathecally, and subcutaneously. Administration of apoptosis-modifying fusion protein composition is indicated for patients with a neurodegenerative disease, suffering from stroke episodes or transient ischemic injury, or experiencing uncontrolled or unwanted cell growth, such as malignancies or neoplasms. More generally, treatment is appropriate for any condition in which it would be beneficial to alter (either inhibit or enhance) an apoptotic response of a subject's target cells. The particular mode of administration and the dosage regimen will be selected by the attending clinician, taking into account the particulars of the case (e.g., the patient, the disease, and the disease-state involved). By way of example, when apoptosis is being generally inhibited over the short term, for instance after transient ischemic neuronal injury, it may be advantageous to administer relatively large doses of fusion protein repeatedly for a few days. In contrast, if apoptosis is being enhanced in specific cell types, for instance in hyper-proliferative cells, it may be of greater benefit to apply a relatively small dose of fusion protein repeatedly, e.g., daily, weekly, or monthly, over a much longer period of treatment.

In addition to their individual use, apoptosis-modifying fusion proteins as disclosed in the current invention may be combined with various therapeutic agents. For instance, an apoptosis-enhancing fusion protein such as Bad-DTTR may be combined with or used in association with other chemotherapeutic or chemopreventive agents for providing therapy against neoplasms or other hyper-proliferative cellular growth conditions. Various such anti-cancer agents are well known to those of ordinary skill in the art. Apoptosis-modifying fusion proteins according to this invention also can be supplied in the form of kits; the construction of kits appropriate for therapeutically active proteins known.

EXAMPLE 1

Construction of Functional Apoptosis-modifying Fusion Proteins

A. Bcl-$x_L$-DTR

The human Bcl-$x_L$ gene from codon 1 through 233 (provided by Dr. Craig Thompson) and the diphtheria toxin gene from codon 384 through 535 (receptor binding domain, DTR), containing mutations in codons 508 and 525, were amplified by PCR so that the DT mutation at codon 525 was mutated to the wild-type by the PCR primer. The two PCR products, Bcl-$x_L$ I -233 and DT384–535 (DTR), were digested with NdeI/NotI and NotI/XhoI restriction enzymes, respectively. Bcl-$x_L$ was fused to the 5' end of the DTR gene with a linker (GCG TAT TCT GCG GCC GCG, SEQ ID NO: 5) to encode for Ala Tyr Ser Ala Ala Ala (SEQ ID NO: 6) between the two peptide domains. The two digested fragments were ligated into the prokaryotic expression vector pET16b (Novagen, Inc., Madison, Wis.) cut with NdeI and XhoI (FIG. 1A). The codon 508 of DTR was mutated to the wild-type form (Phe→Ser) and the first three nucleotides (CAT) of NdeI were deleted by double-stranded, site-directed mutagenesis. FIG 1A shows a schematic representation of the resultant apoptosis-modifying fusion protein, Bcl-$x_L$-DTR.

As controls, human Bcl-$x_L$ (codons 1–233) and DTR (codons 384–535 of DT) genes were separately subcloned into pET16b vectors through NdeI and XhoI sites. The histidine tag and Factor Xa digestion site sequences from the expression vector were upstream of Bcl-$x_L$, DTR and Bcl- $x_L$-DTR coding sequences. All three expression constructs were verified by sequencing.

For expression in eukaryotic cells, Bcl-$x_L$-DTR and Bcl-$x_L$ gene constructs were inserted in the eukaryotic vector pcDNA3 (Invitrogen, Carlsbad, Calif.) and the constructs verified by sequencing.

B. Bad-DTTR

The full-length mouse Bad gene with two Ser→Ala mutations at codons 112 and 136 (Schendel et al., *Proc. Natl. Acad. Sci. USA* 94:5113–5118, 1997), and the diphtheria toxin gene from codons 194 through 535 (translocation and receptor-binding domains, DTTR, without the catalytic domain) were amplified by PCR. The two PCR products, Bad and DT194–535 (DTTR), were used as templates to directly fuse the Bad gene to the 5' end of DTTR gene by a second round of PCR. The Bad-DTTR gene fragment was digested with NdeI and XhoI and ligated into the prokaryotic expression vector pET16b (Novagen, Inc., Madison, Wis.) digested with NdeI and XhoI. The histidine tag and Factor Xa digestion site sequences from the expression vector were upstream of the Bad-D1TR coding sequence. The expression construct was verified by sequencing.

EXAMPLE 2

Expression and Purification of Functional Apoptosis-modifying Fusion Proteins

A. Prokaryotic Expression

To produce proteins for extracellular addition to cells, the Bcl-xi gene, the DTR domain gene and the Bcl-$x_L$-DTR fusion gene were cloned into pET16b. *E. coli* BL2 1 (DE3) strain was used to express Bcl-$x_L$-DTR, Bad-DTTR, Bcl-$x_L$ and DTR, with addition of 1 mM IPTG when the OD260 reached 0.5–0.7. After two hours incubation and lysis by French press the inclusion bodies were collected and dissolved in 6M guanidine-HCl.

B. Eukaryotic Expression

Figure 1B:
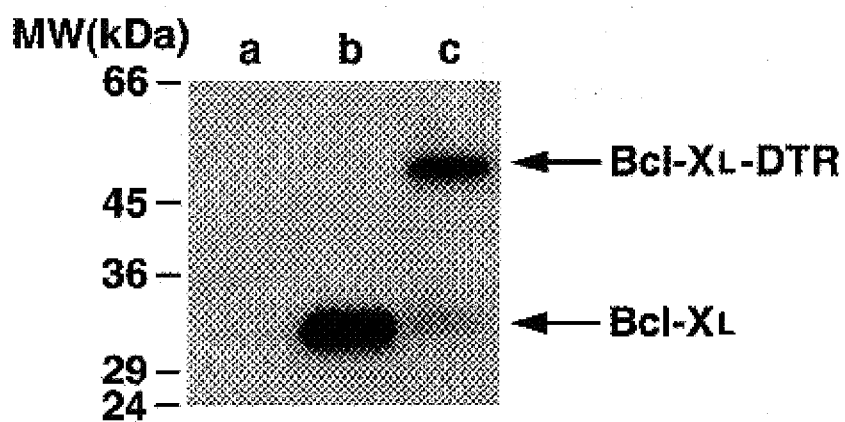

Transfection of HeLa cells with the fusion constructs was performed as reported previously (Wolter et al., *J Cell Biol* 139:1281–1292, 1997). HeLa cells were harvested and lysed in 1 ml buffer containing 100 $\mu$/ml leupeptin 20 hours after transfection, centrifuged to remove cell debris, and 15 $\mu$l aliquots of the supernatant loaded onto 10–20% SDS-PAGE. The plasmid encoded proteins were visualized by immunoblotting with anti-Bcl-$x_L$ monoclonal antibody (2H12, Trevigen, Gaithersburg, Md.) and developed using enhanced chemiluminescence (Amersham Inc., Arlington Heights, Ill.). Results are shown in FIG. 1B.

C. Purification

Histidine tag binding resin (Novagen, Inc., Madison, Wis.) was used to purify Bcl-$x_L$-DTR, Bad-DTTR, Bcl-$x_L$, and DTR. Proteins were refolded by dialysis against, or dilution into, 100 mM Tris-Acetate (pH 8.0)/0.5 M arginine, concentrated with PEG 15,000–20,000 and dialyzed against PBS. This yielded protein purified to greater than 90% homogeneity. The four proteins were subjected to 10–20% SDS-PAGE, visualized by immunoblotting with either anti-Bcl-$x_L$ monoclonal (2H12) or horse anti-DT polyclonal antibodies (Centers for Disease Control, Atlanta, Ga.) and developed as above. They were of the expected molecular weight on SDS PAGE and of the expected immunoreactivity to antibodies against Bcl-$x_L$ or DT on Western blots.

EXAMPLE 3

Assays for Measuring Fusion Protein Binding to, and Translocation Into, Target Cells A. Competitive Binding Assay Protein binding to the diphtheria toxin receptor was performed as previously reported (Greenfield et al, *Science* 238:536–539, 1987) with the following modifications. DT was radiolabeled with $I^{125}$ using iodobeads (Pierce Chem. Co., Rockford, Ill.) as described by the manufacturer. Cos-7 cells, grown to confluency in 12 well costar plates, were analyzed for receptor binding and competition by incubation for three hours on ice. Results are reported in FIG. 2. Cold competitor proteins, native DT (Δ), Bcl-$x_L$-DTR (▲), Bcl-$x_L$ (○), and DTR (●), were used to displace $I^{125}$ labeled DT tracer.

Figure 2:
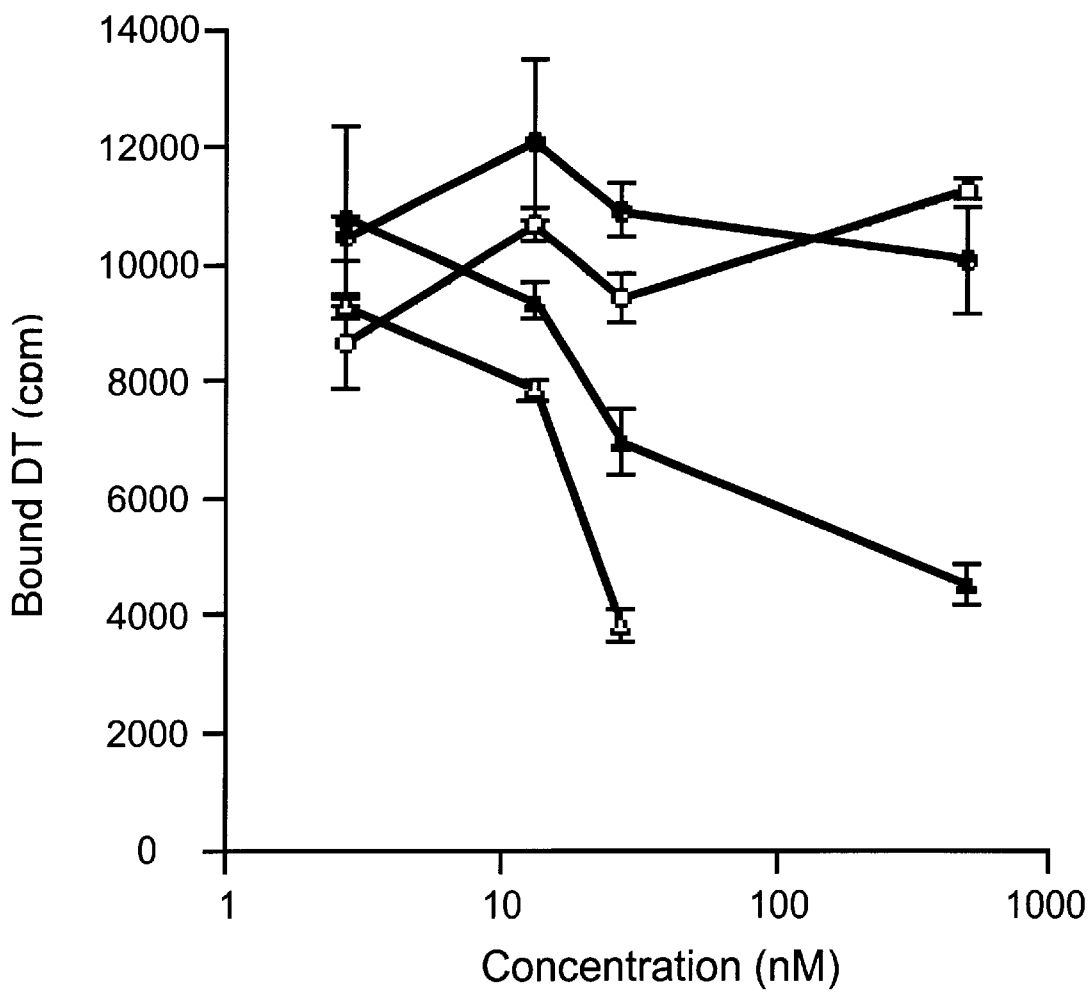
FIG. 2 is a graph that shows the results of a diphtheria toxin receptor competitive binding assay. Cold competitor proteins [native DT (△), Bcl-$x_L$-DTR (▲), Bcl-$x_L$ (○), and DTR (●)] were used to displace I$^{125}$ labeled diphtheria toxin (DT) tracer, and the amount of bound, labeled tracer was measured. Native DT and the fusion protein Bcl-$x_L$-DTR compete for DT receptor binding in the nanomolar concentration range.

Native DT and Bcl-$x_L$-DTR compete for DT receptor binding in the nanomolar concentration range. DT and the Bcl-$x_L$-DTR fusion protein competed for $I^{125}$-DT binding to its receptor to a similar extent although the affinity of the fusion was three times lower than that of native DT (FIG. 2). Neither the Bcl-$x_L$ domain alone nor the DTR domain alone was able to compete for DT receptor binding. The more complete protein (Bcl-$x_L$-DTR), where Bcl-$x_L$ is substituted for the DT translocation domain, folded such that DT receptor binding activity was retained whereas the isolated binding domain (DTR) did not. Addition of the DT A chain domain to the N-terminus of Bcl-$x_L$-DTR further increased the affinity of the chimera to the DT receptor.

B. Assays for Effective Transport of the Fusion Protein Into the Target Cell

Diphtheria toxin is endocytosed by cells and reaches low pH intracellular compartments. The low pH triggers a conformational change in the translocation domain, which allows this domain to insert into membranes and form channels. The toxicity of DT is blocked by lysosomotropic agents such as chloroquine, which increase the pH of intracellular compartments. Chloroquine at a concentration that blocks diphtheria toxin toxicity (10 $\mu$M) did not block the activity of Bcl-$x_L$-DTR to inhibit poliovirus-induced cell death. Thus, the mechanism of membrane interaction of Bcl-$x_L$-DTR differs to some extent from that of DT. However, brefeldin A, an inhibitor of vesicle traffic between the ER and the Golgi apparatus (Lippincott-Schwartz et al., *Cell* 67:601–616, 1991; Hunziker et al., *Cell* 67:617–627, 1991), does block the anti-apoptosis activity of Bcl-$x_L$-DTR (Table 3). These results indicate that Bcl-$x_L$-DTR must be endocytosed and suggest that Bcl-$x_L$-DTR must reach the Golgi apparatus or the ER to prevent cell death. The subcellular location from which native Bcl-2 family members regulate apoptosis is currently under scrutiny (Hunziker et al., *Cell* 67:617–627, 1991). Several intracellular membrane locations, including the ER, appear able to mediate Bcl-2 family regulation of cell death (Krajewski et al., *Cancer Res.* 53:4701–47 14, 1993). Bcl-$x_L$-DTR may reach the ER to translocate into the cell cytosol or perhaps Bcl-$x_L$-DTR, when bound closely to a membrane, can insert into that membrane and inhibit apoptosis in the membrane-intercalated form.

EXAMPLE 4

Measurement of Bcl-$x_L$-DTR Apoptosis-inhibiting Activity

A. Apoptosis Inhibition After Transient Cell Transfection

To demonstrate that Bcl-$x_L$-DTR is effective at inhibiting apoptosis when expressed from within the target cell, this construct and the control construct containing Bcl-$x_L$ were transiently transfected into HeLa cells. Assay of apoptosis inhibition after transient transfection was performed as reported previously (Wolter et al., *J. Cell Biol.* 139:1281–1292, 1997). The Bcl-$x_L$-DTR fusion gene blocked apoptosis after transient transfection into HeLa cells (FIG. 1C) to an extent similar to that of the Bcl-$x_L$ gene after C-terminal tail truncation (Wolter et al., *J Cell Biol* 139:1281–1292, 1997).

Figure 3A:
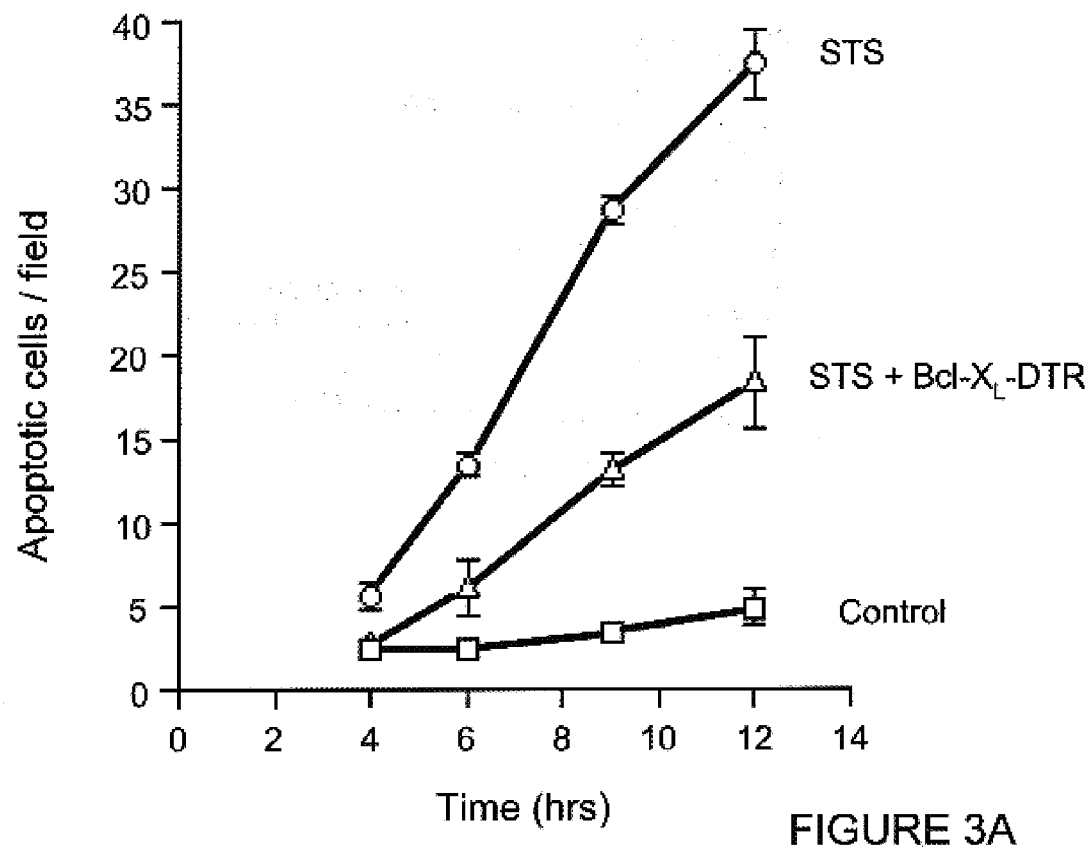
FIGS. 3A–B depicts the results of several experiments that demonstrate the apoptosis-inhibiting character of the fusion construct Bcl-$x_L$-DTR. Panel A is a graph of a time course of apoptosis induced by staurosporine (STS). Cells were treated with 0.1 μM STS (○), 0.1 μM STS plus 4.8 μM Bcl-$x_L$-DTR protein medium (△), or 20 μl of PBS (□). Results are presented as the average number of apoptotic cells per field (magnification 160×). For each point, at least 5 fields were counted in each of at least 3 wells.

B. Inhibition of STS-induced Apoptosis by Extracellular Treatment With Bcl-$x_L$-DTR Hoechst dye no. 33342 staining: The effectiveness of extracellular delivery of Bcl-$x_L$ or the Bcl-$x_L$-DTR fusion protein for inhibiting the rate of cell death by apoptosis was examined as follows. Cos-7 cells at $3\times10^4$ cells/cm$^2$ in 100 $\mu$l DMEM with 10% FBS were incubated with 0.1 $\mu$M STS (○), 0.1 $\mu$M STS plus 4.8 $\mu$M Bcl-$x_L$-DTR protein added to the medium (Δ) or 20 $\mu$l of PBS (□). Apoptotic cells were quantified by staining with Hoechst dye no. 33342. Results in FIG. 3A are presented as the average number of cells per field (magnification 160×). For each point, at least 5 fields were counted in each of at least 3 wells. Bcl-$x_L$-DTR dramatically decreased the rate of apoptosis in Cos-7 cells. Six different preparations of Bcl-$x_L$-DTR were found to have activity and the apoptosis prevention activity was stable for at least 5 months when Bcl-$x_L$-DTR was stored at 4° C. Addition of Bcl-$x_L$-DTR minutes before the addition of STS blocked more than 70% of Cos-7 cell death after 6 hours and more than 50% of cell death after 12 hours of STS exposure (FIG. 3A).

Jurkat, HeLa and U251 cells were also protected from STS-induced apoptosis by Bcl-$x_L$-DTR (Table 2). Bcl-$x_L$ protein added to Cos-7 cells, however, did not alter the extent of cell death induced by STS. A nontoxic DT mutant able to bind the DT receptor, CRM 197, also had no effect on apoptosis induced by STS. To further test the role of DT receptor binding in apoptosis inhibition, cells expressing DT receptors were compared with cells lacking DT receptors. Mouse and rat cells are thousands of times less sensitive to DT than human or monkey cell lines due to a lack of the DT receptor (Pappenheimer *The Harvey Lectures* 76:45–73, 1982). Comparing human, monkey, mouse and rat cell lines revealed that those cells lacking the DT receptor, WEHI-7.1 and 9L, were insensitive to apoptosis protection by Bcl-$x_L$-DTR (Table 2). The sensitivity of the six cell lines to DT toxicity, thought to reflect DT receptor levels, correlated with sensitivity to apoptosis prevention by Bcl-$x_L$-DTR (Table 2).

Figure 1C:
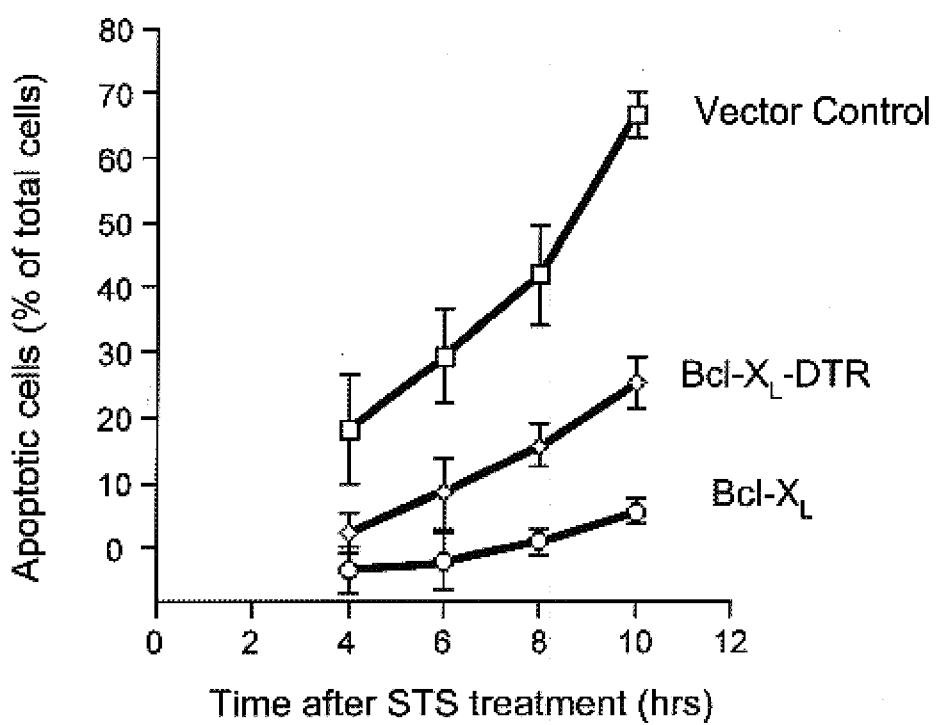

The magnitude of apoptosis inhibition by extracellular Bcl-$x_L$-DTR (FIG. 3A, Table 2) was similar to that found by transfection of the fusion gene into cells (FIG. 1C). Although fusion to the C-terminus of Bcl-$x_L$ inhibited bioactivity relative to native Bcl-$x_L$ after transfection (FIG. 1C), a very substantial prevention of cell death was obtained at both the gene level and the protein level (FIG. 3A). Thus the delivery of Bcl-$x_L$-DTR is efficient and apoptosis can be prevented by delivery of Bcl-$x_L$ from the outside of cells.

Figure 3B:
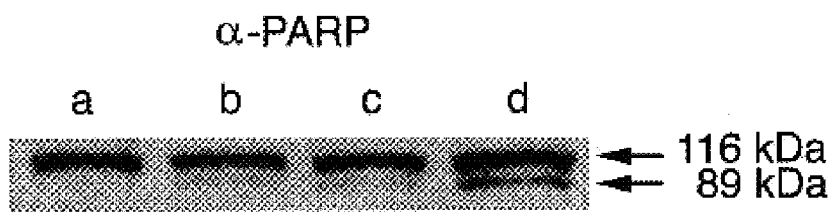

Measurement of caspase activity: To confirm the results of cell death measurements by Hoechst staining and trypan blue dye exclusion, we examined caspase-induced cleavage of poly-ADP ribose polymerase (PARP). HeLa cells were plated in EMEM containing 10% FBS at $2\times10^5$ cells/ml and treated with two different preparations of Bcl-$x_L$-DTR at 1.48 $\mu$M or 1 $\mu$M. Fifteen hours later, cells were treated again with Bcl-$x_L$-DTR at 1.48 $\mu$M or 1 $\mu$M. Immediately after the second treatment, 0.8 $\mu$M STS was added. Three hours later, cell lysates were made and aliquots were loaded onto SDS-PAGE, immunoblotted with anti-PARP polyclonal antibody (Boehringer Mannheim GmbH, Germany) and developed with enhanced chemiluminescence. Lane a contains control HeLa cells not incubated with STS (uninduced cells); Lane b, HeLa cells treated with STS plus 1 $\mu$M Bcl-$x_L$-DTR protein; Lane c, HeLa cells treated with STS plus 1.48 $\mu$M Bcl-$x_L$-DTR protein; and Lane d, HeLa cells treated with STS and no fusion protein. HeLa cells incubated with Bcl-$x_L$-DTR showed significantly less cleavage of PARP after apoptosis induction with STS (FIG. 3B).

Figure 4A:
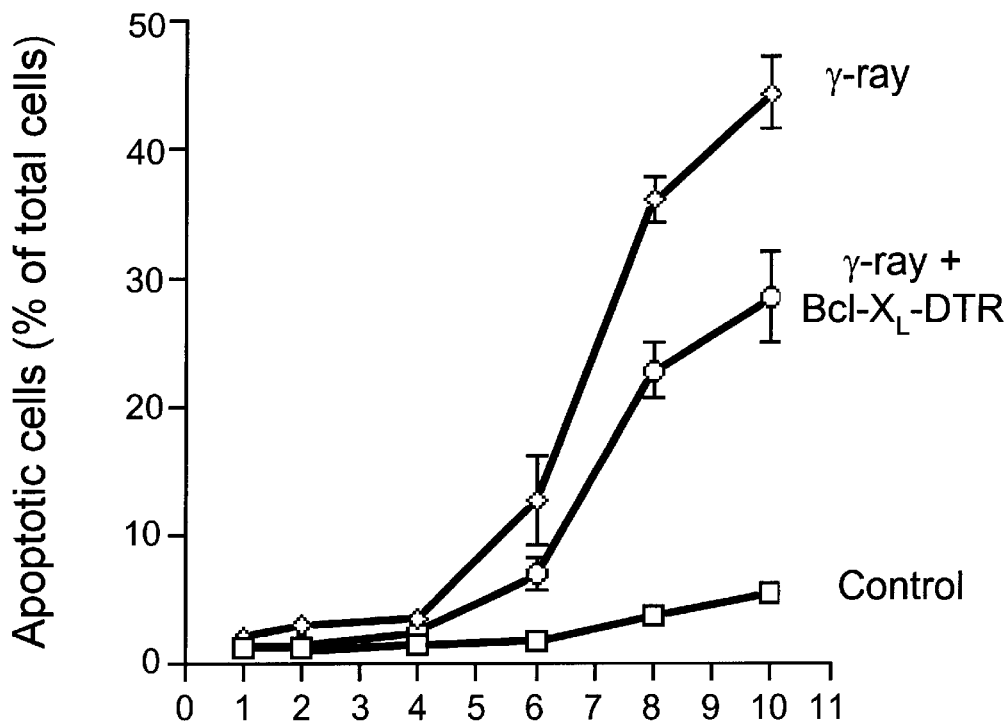
FIGS. 4A–B shows that Bcl-$x_L$-DTR inhibits of apoptosis induced by γ-radiation, but not that induced by α-Fas antibody.

C. Inhibition of γ-radiation-induced Apoptosis by Extracellular Treatment With Bcl-$x_L$-DTR Radiation is a potent inducer of apoptosis in many hematopoetic cell types. The ability of Bcl-$x_L$-DTR to prevent radiation-induced apoptosis was examined in the human T cell line, Jurkat. When added to the media (serum-free RPMI-1640 medium with insulin and transferrin) of Jurkat cells plated at $10^5$ cells/ml a few minutes prior to induction of apoptosis by 10 gray γ-radiation, Bcl-$x_L$-DTR (4.63 $\mu$M) blocked almost half of the ensuing cell death (FIG. 4A). Apoptotic cells were counted using Hoechst dye no. 33342. Control cells were not irradiated and not treated with Bcl-$x_L$-DTR.

In a clonogenic assay measuring long term survival, Jurkat cells showed more than a 3-fold greater survival when Bcl-$x_L$-DTR was added to the media immediately prior to 5 gray γ-radiation.

Figure 4B:
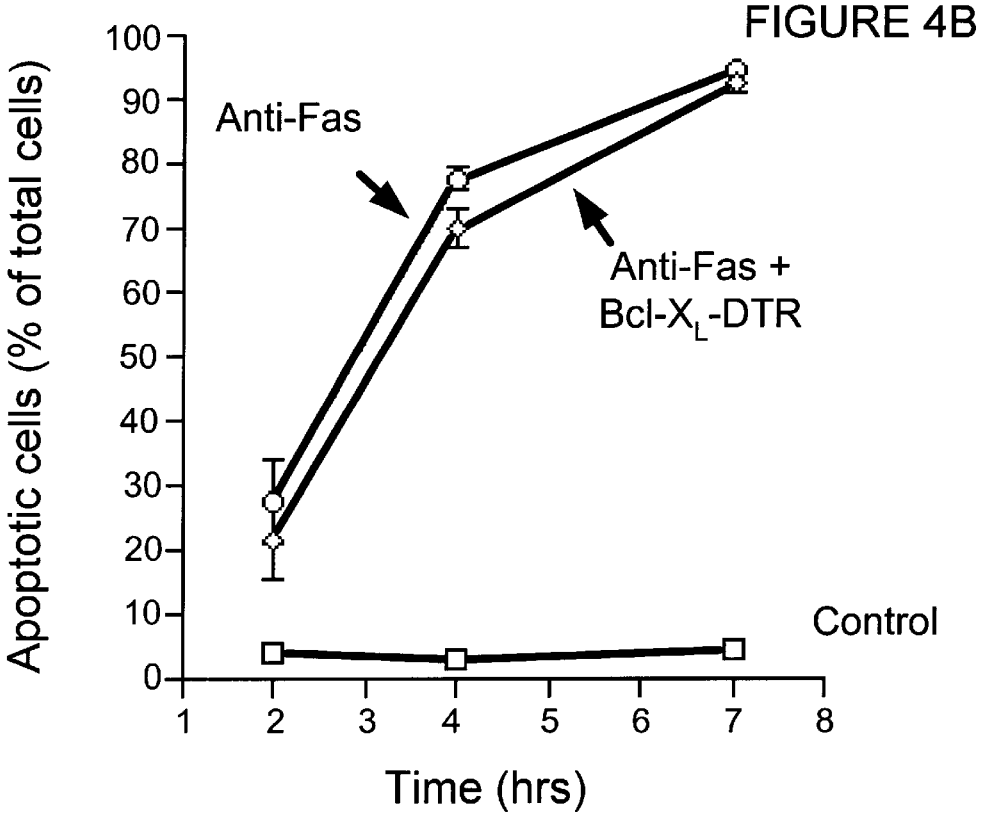

D. Inhibition of Anti-Fas-induced Apoptosis by Extracellular Treatment With Bcl-$x_L$-DTR Jurkat cells are also sensitive to apoptosis induced by antibody binding to the Fas/APO-1/CD95 receptor. The Fas pathway of apoptosis is one of the few pathways shown to be less sensitive or insensitive to apoptosis protection by Bcl-2 and Bcl-$x_L$ (Boise & Thompson *Proc. Natl. Acad. Sci. USA* 94:3759–3764, 1997; Memon et al., *J. Imunol.* 155:4644–4652, 1995) and contrasts with radiation-induced apoptosis in this regard. Jurkat cells were plated at $10^5$ cells/ml in serum-free RPMI-1640 medium with insulin and transferrin, and treated with 100 ng/ml anti-Fas antibody (CH11, Upstate Biotechnology, Lake Placid, N.Y.) minutes after addition of Bcl-$x_L$-DTR to a concentration 4.68 $\mu$M. Control cells were treated with PBS and no anti-Fas antibody. Fas antigen-induced apoptosis (measured by counting dying cells using Hoechst dye no. 33342) showed very little inhibition by Bcl-$x_L$-DTR, although there was a statistically significant decrease in apoptosis between 2 and 4 hours in some experiments (FIG. 4B). The degree of protection of different apoptosis pathways by extracellular Bcl-$x_L$-DTR corresponded with that seen by transfection with the Bcl-$x_L$, gene.

E. Inhibition of Poliovirus-induced Apoptosis by Extracellular Treatment With Bcl-$x_L$-DTR Viruses induce a powerful apoptosis response in certain cells and prevention of this apoptosis may have therapeutic utility (Hardwick, *Adv. Pharm.* 41:295–336, 1997). Poliovirus-induced apoptosis of HeLa cells was also examined for sensitivity to extracellular Bcl-$x_L$-DTR, a system where inhibition of cell death by transfection with the Bcl-$x_L$ gene has been demonstrated (Castelli et al., *J Exp. Med.* 186:967–972, 1997). Adding Bcl-$x_L$-DTR 30 minutes after infection of cells with low titers (MOI of 1 pfu/cell) of poliovirus (FIG. 5) or with moderately high titers (MOI of 20 pfu/cell) of poliovirus prevented more than half of the cell death for up to 24 hours. Addition of extracellular Bcl-$x_L$ or the DTR domain proteins alone had no affect on poliovirus-induced apoptosis.

F. Competition of Apoptosis Inhibition

Caspase inhibitors block many pathways of apoptosis and are being explored for pharmacologic potential to inhibit cell death (Chen et al., *Nature* 385:434–439, 1997). zVAD-fmk and Boc-D-fink are powerful, broad specificity caspase inhibitors that block many apoptosis pathways (Henkart, *Immunity* 4:195–201, 1996). Apoptosis inhibition activity of zVAD-fmk and Boc-D-fmk was compared with that of Bcl-$x_L$-DTR. HeLa cells were plated at a density of $1 \times 10^5$ cells/well in EMEM containing 10% FBS and antibiotics, infected with poliovirus at an MOI of 1 pfu/cell as reported previously (Castelli et al., *J Exp Med* 186:967–972, 1997) and immediately treated with negative control peptide zFA-fmk at 20 $\mu$M, Bcl-$x_L$-DTR at 0.48 $\mu$M, or peptides zVAD-fmk or Boc-D-fink at 20 $\mu$M. Cell viability was assessed by trypan blue dye exclusion 24 hours following addition of virus. zFA-fmk, zVAD-fmk and Boc-D-fmk were from Enzyme Systems Products, Dublin, Calif.

Figure 5:
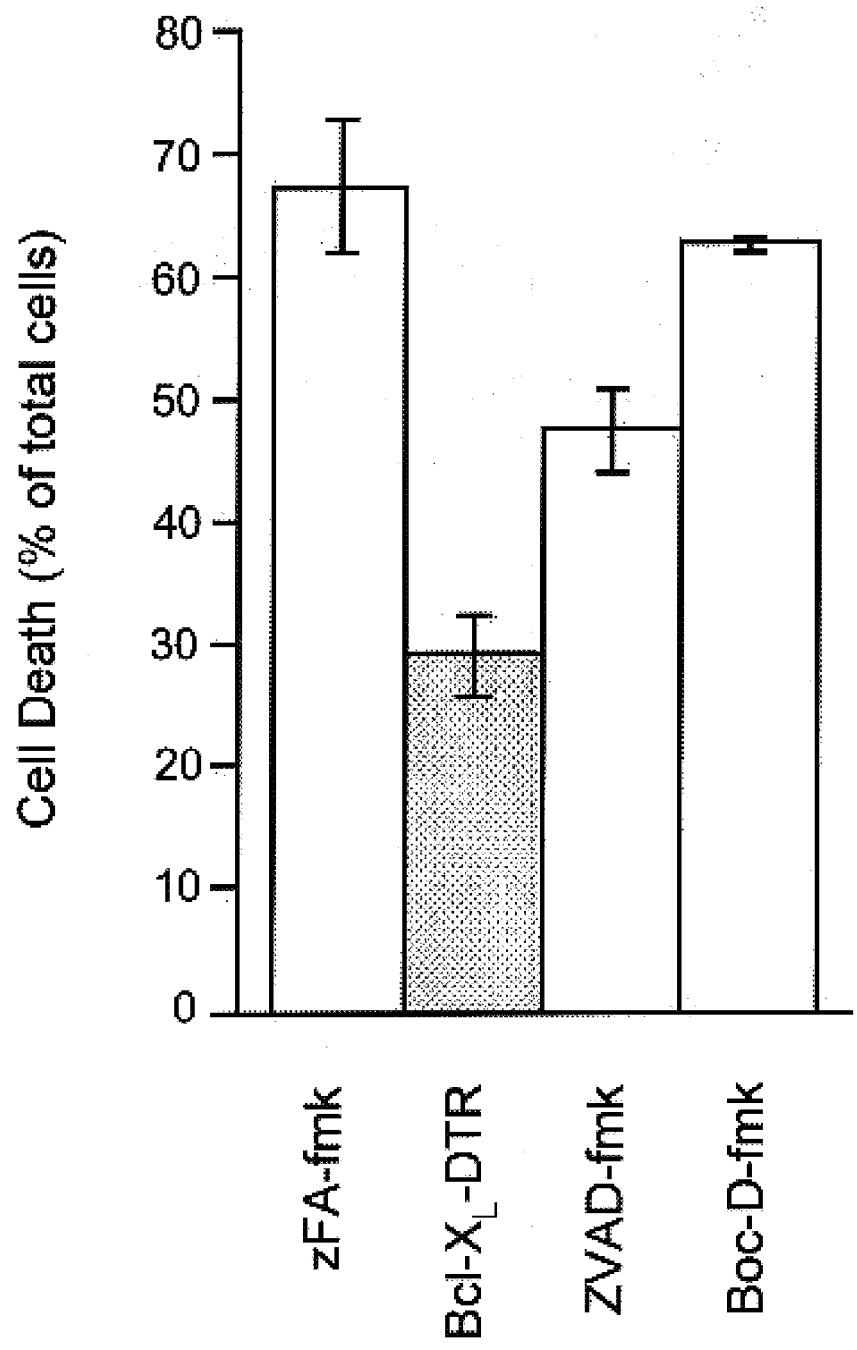
FIG. 5 shows that Bcl-$x_L$-DTR inhibits apoptosis induced by poliovirus.

Bcl-$x_L$-DTR at 0.48 $\mu$M blocked cell death to a greater extent than either zVAD-fmk or Boc-D-fmk at 20 $\mu$M (FIG. 5). Bcl-$x_L$-DTR showed a strong inhibition of a potent and pathologically important apoptosis pathway. Interestingly, Bcl-$x_L$ appears to act at an early step in the cell death pathway when intervention can permit long term viability of cells, whereas caspase inhibitors appear, to work relatively more downstream in the apoptosis pathway (Chinnaiyan et al., *J Biol Chem* 271:4573–4576, 1996; Xiang et al., *Proc. Natl. Acad. Sci. USA* 93:14559–14563, 1996; Miller et al, *J. Cell Biol* 139:205–217, 1997).

EXAMPLE 5

Measurement of Bad-DTTR Apoptosis-enhancing Activity

A. Stimulation of Apoptosis by Extracellular Treatment With Bad-DTTR

Figure 6:
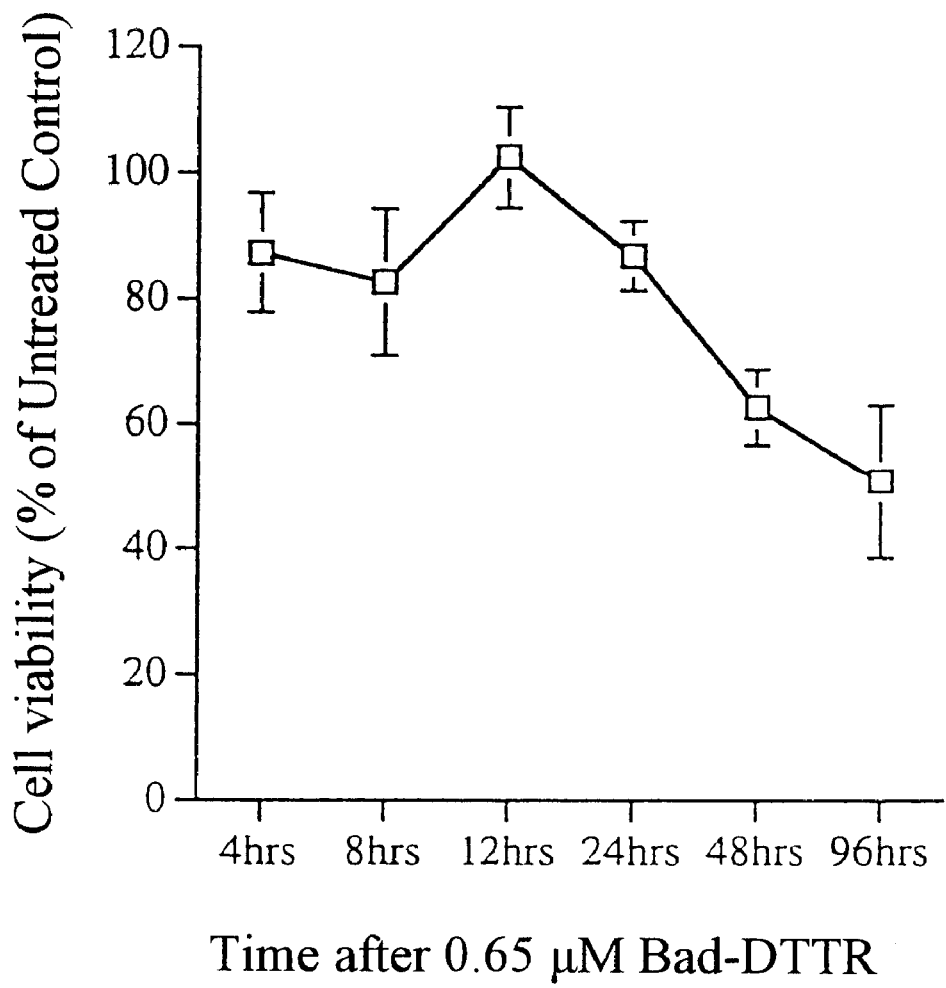
FIG. 6 is a graph showing the time course of viability of cells treated with Bad-DTTR.
Figure 7A:
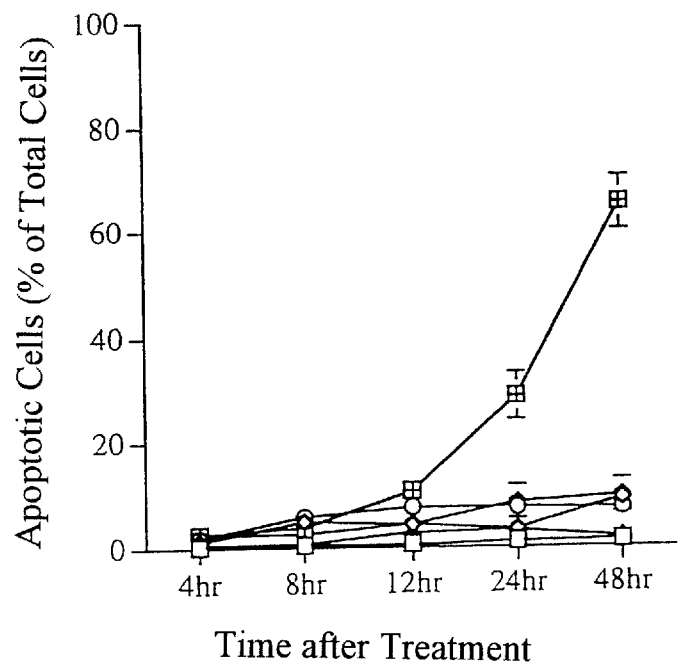
FIGS. 7A–B shows the results of experiments that demonstrate that Bad-DTTR combined with STS triggers massive cell death.
Figure 7B:
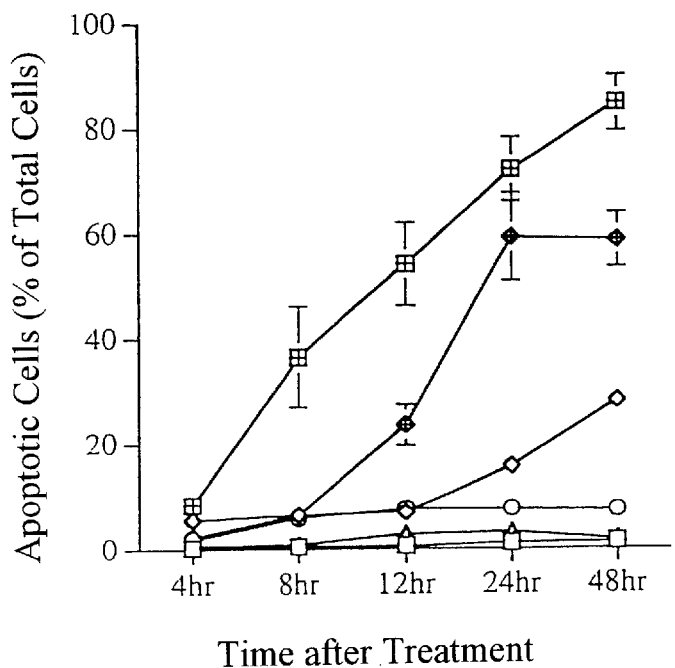

To determine the effectiveness of the fusion protein Bad-DTR at triggering apoptosis, cell survival after exposure to Bad-DTTR was examined. U251 MG cells at $3 \times 10^4$ cells/$cm^2$ in 100 $\mu$l DMEM with 10% FBS were incubated with 0.65 $\mu$M Bad-DTTR protein added to the medium or 20 $\mu$l of PBS. Total and apoptotic cells were quantified by staining with Hoechst dye no. 33342. Results are presented in FIG. 6 as the average number of cells per field (magnification 160x). Bad-DTR decreases cell viability 12 hours after treatment.

B. Enhancement of STS-triggered Apoptosis by Extracellular Treatment With Bad-DTTR To examine the ability of Bad-DTR to enhance apoptosis triggered by STS, cell survival was determined after exposure to various concentrations of STS, in combination with various combinations of Bad-DTR. U251 MG cells at $3 \times 10^4$ cells/$cm^2$ in 100 $\mu$l DMEM with 10% FBS were treated with PBS, 0.1 $\mu$M STS, 0.65 $\mu$M Bad-DTR, 0.065 $\mu$M Bad-DTTR, 0.1 $\mu$M STS plus 0.65 $\mu$M Bad-DTR and 0.1 $\mu$M STS plus 0.065 $\mu$M Bad-DTTR. Apoptotic death cells were quantified at different times by staining with Hoechst dye no. 33342. Results are presented as the average number of cells per field (magnification 160x). Apoptosis is most enhanced when cells are treated with 0.1 $\mu$M STS plus 0.65 $\mu$M Bad-DTR, and cells begin to die about 12 hours after treatment.

U251 MG cells at $3 \times 10^4$ cells/$cm^2$ in 100 $\mu$l DMEM with 10% FBS were treated with PBS, 1 $\mu$M STS, 0.65 $\mu$M Bad-DTTR, 0.065 $\mu$M Bad-DTTR, 1 $\mu$M STS plus 0.65 $\mu$M Bad-DTTR and 1 $\mu$M STS plus 0.065 $\mu$M Bad-DTTR. Apoptotic cells were quantified and presented as above. The combination of 1 $\mu$M STS and Bad-DTTR at various concentrations causes an earlier onset of apoptosis in U251 MG cells.

EXAMPLE 6

$LF_n$-Bcl-$x_L$ Inhibits Neuron, Macrophage, and Lymphocyte Apoptosis

Anthrax toxin includes three components: lethal factor (LF), edema factor (EF) and protective antigen (PA) (Leppla, Anthrax toxin. In *Handbook of Natural Toxins*, Moss et al., Eds., Dekker, N.Y., Vol. 8, pp. 543–572, 1995). PA binds simultaneously to LF and to a cell surface receptor existing on the cells of almost all species including rodents (Leppla, 1995: Friedlander, *J. Biol Chem.* 261:7123–7126, 1986), and transports LF into cells where LF causes toxic effects. PA alone, however, is not toxic. It has been found that the first 255 residues ($LF_n$) of LF, which constitute the PA-binding domain and are not toxic to cells, are sufficient for delivery of heterologous peptides to the cytosol. Cytotoxins have been fused to $LF_n$ (Leppla, 1995; Arora et al., *J Biol. Chem.* 269:26165–26171, 1994; Milne et al., *Mol. Microbiol.* 15: 661–666, 1995). Administration of a fusion protein containing $LF_n$ and the gp120 envelope glycoprotein of HIV-1 along with PA to antigen-presenting cells sensitized them to cytolysis by cytotoxic T-lymphocytes (CTL) specific to gp120 (Goletz et al., *Proc Natl Acad Sci USA* 94:12059–12064, 1997). In vivo, $LF_n$-fused to CTL epitopes injected along with PA has been shown to stimulate a CTL response against the antigens in mice (Ballard et al., *Proc. Natl. Acad. Sci. USA* 93: 12531–12534, 1996; Ballard et al., *Infect. Immun.* 66.615–619, 1998; Ballard et al., *Infect Immun.* 66:4696–4699, 1998; Doling et al., *Infect. Immun.* 67: 3290–3296, 1999).

To inhibit neuron apoptosis, another protein delivery system was engineered by fusing a nontoxic domain of anthrax toxin to Bcl-$x_L$, to create the $LF_n$-Bcl-$x_L$ chimeric fusion protein. Macrophage and lymphocyte death in culture, and neuron death in vivo in a retinal ganglion cell model of apoptosis induced by axotomy, can be prevented by application of this fusion protein.

A. Construction of $LF_n$-Bcl-$x_L$ in a Prokarvotic Expression Plasmid

The coding sequence for lethal factor (LF) from codons 34 to 288 ($LF_n$) (Bragg et al., *Gene 81:45–54, 1989*), which is the amino-terminal domain (residues 1–255) of mature LF (Leppla, 1995), was amplified using PCR with the template of pET15b/$LF_n$ (Milne et al., *Mol. Microbiol.* 15: 661–666, 1995). The gene of human Bcl-$x_L$ from Codons 1 to 209 (Bcl-$x_L$ (1–209)) (Boise et al., *Cell* 74: 597–608, 1993) was amplified by PCR. Then the $LF_n$ encoding sequence was fused to the 5' end of Bcl-$x_L$(1–209) encoding sequence by a second round of PCR. A stop codon was introduced immediately after Codon 209 of Bcl-$x_L$. The fused DNA fragment, $LF_n$-Bcl-$x_L$, was cut with NdeI and Xho I, and inserted into prokaryotic expression vector pET15b cut with Nde I and Xho I (FIG. 8). A histidine tag and thrombin cleavage site were linked to the N-terminal of $LF_n$-Bcl-$x_L$. Similarly, the Bcl-$x_L$ gene from codons 1 to 209 was also genetically inserted into pET15b at the sites of Nde I and Xho I. All the constructs were verified by DNA sequencing.

B. Construction of Eukaryotic Expression Plasmids, Transfection, Western Blotting and Biologic Activity Assay The sequences encoding $LF_n$-Bcl-$x_L$, Bcl-$x_L$ from codons 1 to 209, and full-length Bcl-$x_L$, were separately engineered into eukaryotic expression vector pcDNA3.1+ and verified by DNA sequencing. Cos-7 cells were co-transfected with plasmid EGFP-C3 and one of the three plasmids as reported (Keith et al., *J Cell Biol* 139: 1281–1292, 1997). The cells were treated with 0.1 $\mu$M staurosporine (STS) 12 hours later. The dead and living cells were counted with Hoechst 33342 at different times after STS treatment (Liu et al., *Proc Natl Acad Sci USA* 96: 9563–9567, 1999; Keith et al., *J Cell Biol* 139: 1281–1292, 1997). The cells were harvested and lysed 20 hours after transfection, and aliquots were loaded onto SDS/10–20% PAGE gels. The plasmid-encoded proteins were visualized by immunoblotting with anti-Bcl-$x_L$ mAb (Trevigen, Gaithersburg, Md.) and developed by using enhanced chemiluminescence (Amersham Pharmacia).

C. Protein Expression, Purification, SDS-PAGE and Western Blotting

The proteins $LF_n$, $LF_n$-Bcl-$x_L$ and Bcl-$x_L$ from codons 1 to 209 were individually expressed in *E. coli* BL21 (DE3) (Novagen, Inc.) and purified with a His·Tag binding purification kit (Novagen, Inc.). The transformed BL21 (DE3) was cultured at 37° C. in LB medium until the OD600 reached 0.5–0.8, and treated with 1 mM IPTG, and then cultured for 3 more hours. The cells was pelleted, suspended in 1×His·Tag binding buffer with 1 mM phenylmethylsulfonyl fluoride (PMSF), 1 mM aprotinin and 1 mM leupeptin, and disrupted with French Press. The cytosol was separated from cell debris and undisrupted cells by centrifugation at 20,000×g for 30 minutes and loaded on the His·Tag binding column. The eluted proteins were dialyzed against 1×PBS and sterilized with 0.22-um filter. Protective antigen (PA) was purified as reported (Milne et al., *Mol. Microbiol.* 15: 661–666, 1995). The proteins were run on SDS-PAGE gels, and stained with Coomassic Blue or visualized by immunoblotting with anti-Bcl-$x_L$ antibody, and developed as above.

D. J744 Macrophage-like Cell Culture, Treatment and Apoptosis Assay

J744 macrophage-like cells at $10^5$/ml were placed in 96-well plates (100 μl per well), and cultured overnight in RPMI 1640 with 10% FCS. The cells were treated with PBS, 0.1 μM staurosporine alone or 0.1 μM staurosporine along with the different combinations of the proteins $LF_n$-Bcl-$x_L$ (28 μg/ml), PA (33 μg/ml), $LF_n$ (28 μg/ml) and Bcl-$x_L$ (28 μg/ml). The apoptotic and living cells were counted with Hoechst dye no. 33342 as reported (Liu et al., *Proc Natl Acad Sci USA* 96: 9563–9567, 1999).

E. Optic Nerve Section and Intra-ocular Protein Injection

The P0 pups of Fisher 344 rat strain were used for the present study. P0 is defined as the day of birth. The intracranial lesion of unilateral optic nerve was performed as reported (Rabachi et al., *J Neurosci.* 14: 5292–301, 1994). Briefly, a P0 pup was anesthetized by hypothermia. Under a dissecting microscope, an incision over the right eye was cut and a piece of bone flipped up. The right optic nerve was sectioned after suctioning the overlying cerebral cortex. The section site of optic nerve is about 3 mm away from the eyeball. A piece of gelfoam was put in the hole, and the flipped bone replaced, and the incision repaired with SUPERGLUE™. Immediately after the operation, seven, ten and four mice were respectively treated with administration of PBS, $LF_n$-Bcl-$x_L$ (0.65 μg) plus PA (0.35 μg) and PA (0.35 μg) in a volume of 350 nanoliters (nl) per eye through ora serrata into the posterior chamber of the right eyes by using a micro-injector with a pulled micropipette. The pups were warmed up with a light lamp until the recovery, and then sent back to the mother. Four pups from the same litters, which were not operated and not treated, were used for normal control.

F. Histology

Figure 12:
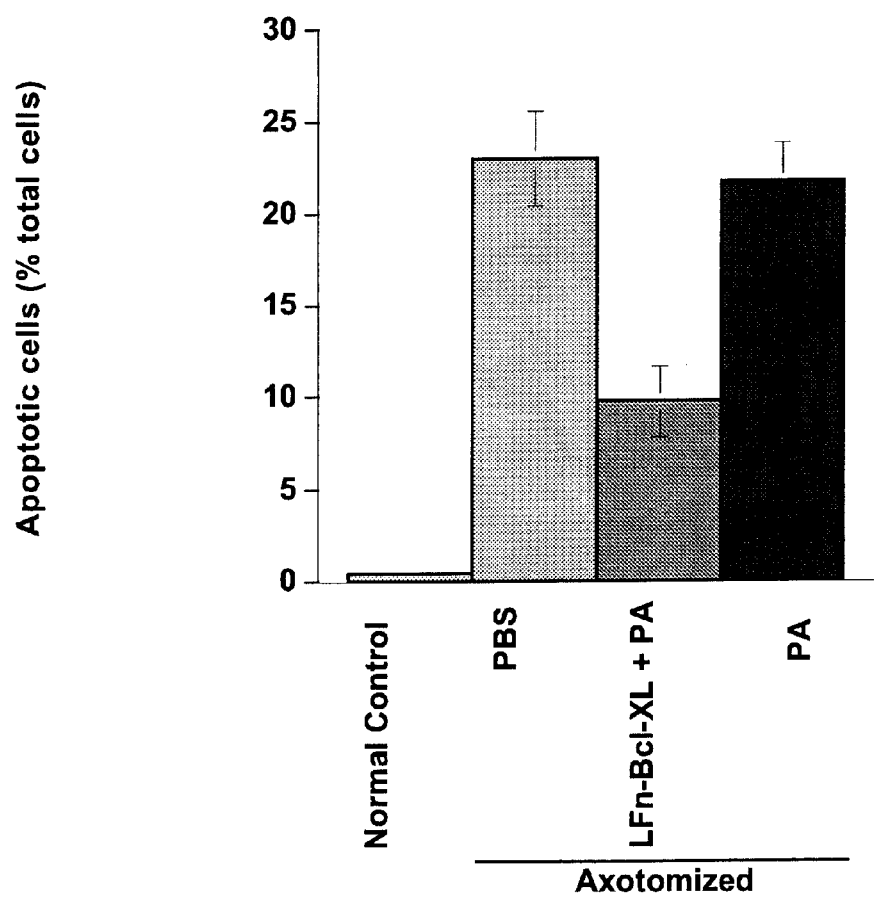
FIG. 12 is a bar graph showing that the fusion protein $LF_n$-Bcl-$x_L$ prevents apoptosis by in neonatal rat retinal ganglion cells 24 hours after optic nerve section. The apoptotic and living cells in retinal ganglion layers were counted 24 hours after optic nerve section immediately followed by the injection of PBS or the indicated protein(s). The percentage of apoptotic cells versus total retinal ganglion cells per retina is represented.

About 24 hours after sectioning of the optic nerve, the right eyes were removed under deep anesthesia with sodium pentobarbital, fixed in 4% paraformaldehyde for approximately 30 hours, embedded in paraffin and cut at 6 μm. The eyes taken from the normal pups in the same litters were processed in the same way to serve as controls. The sections were rehydrated, stained with 0.2% cresyl violet, dehydrated, and mounted with DPX mountant. The number of pyknotic cells and the number of living cells were counted by the use of 40× objective in the entire retinal ganglion cell layer of three sections per retina. The pyknotic cells were identified as reported (Rabachi et al., *J. Neurolsci.* 14: 5292–301, 1994). The values were presented as the percentage of pyknotic cells versus total cells per retina (FIG. 12).

G. Results

The PA protein from the Anthrax bacillus binds cell receptors and can mediate the delivery of the anthrax LF protein to the cell cytosol where LF effects toxicity to cells. The N-terminal domain of LF binds to PA. When exogeneous peptides are fused to the N-terminal domain of LF ($LF_n$), they can be delivered to the cell cytosol by PA. Deletion of the C-terminal region of LF prevents toxicity to cells. To deliver Bcl-$x_L$ to cells, the N-terminal 255 amino acids of 11.1; were fused to Bcl-$x_L$, without including the C-terminal 24 hydrophobic amino acids of Bcl-$x_L$, as shown schematically in FIG. 8. The nucleotide and amino acid sequences of the fusion protein, $LF_n$-Bcl-$x_L$, are shown in SEQ ID NOs: 7 and 8. The fusion protein was expressed in *E. coli* and purified to near homogeneity.

Figure 9:
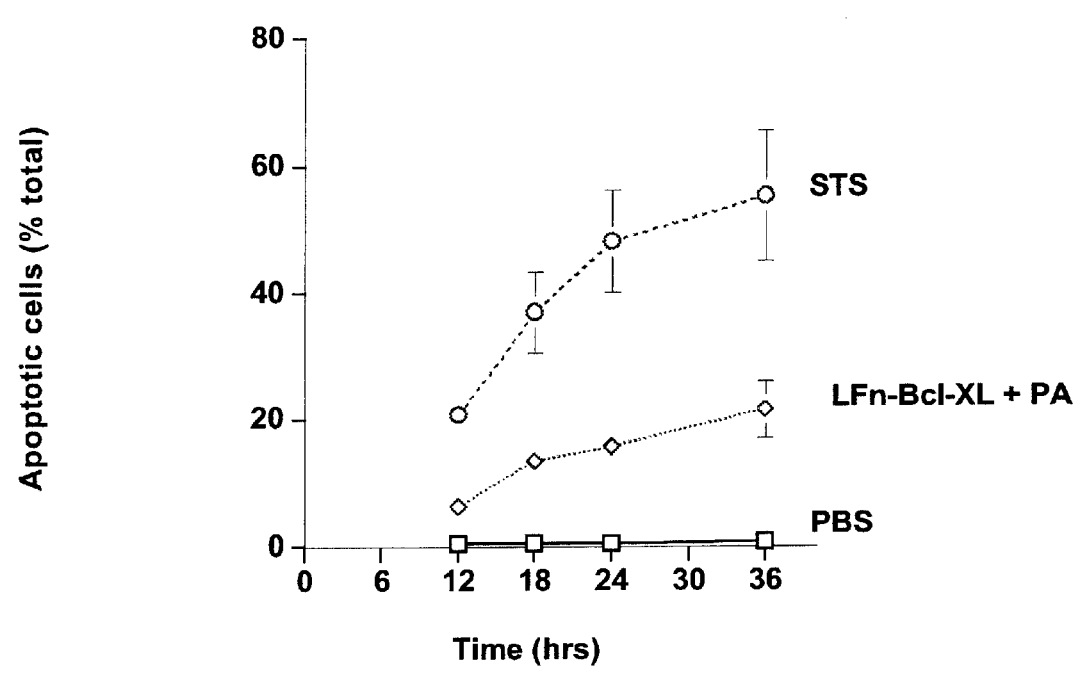

The bioactivity of the $LF_n$-Bcl-$x_L$ was explored in J774 cells in tissue culture. $LF_n$-Bcl-$x_L$, at 28 micrograms per ml plus PA at 33 micrograms per ml was added to the media of cells at the time of apoptosis induction with 0.1 μM staurosporine (STS). Cells treated with staurosporine alone died by apoptosis over the following 36 hours as shown in FIG. 9. When the cells were treated with $LF_n$-Bcl-$x_L$ plus PA, most of the cell death was inhibited.

Figure 10:
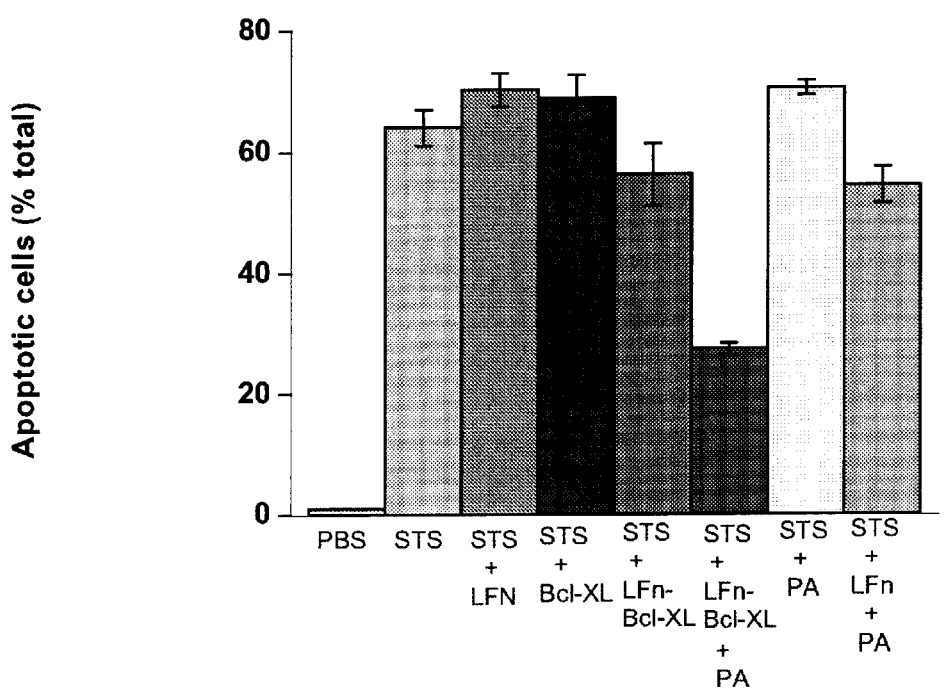
FIG. 10 is a bar graph showing the effect of $LF_n$-Bcl-$x_L$ against J774 treated with STS. J774 cells at $10^4/cm^2$ were treated with PBS, 0.1 μM staurosporine alone, 0.1 μM staurosporine along with $LF_n$ (28 μg/ml), 0.1 μM staurosporine along with Bcl-$x_L$ (28 μg/ml), 0.1 μM staurosporine along with $LF_n$-Bcl-$x_L$ (28 μg/ml), 0.1 μM staurosporine along with $LF_n$-Bcl-$x_L$ (28 μg/ml) plus PA (33 μg/ml), 0.1 μM staurosporine along with PA (33 μg/ml) and 0.1 μM staurosporine along with $LF_n$ (28 μg/ml) plus PA (33 μg/ml). The apoptotic and living cells were stained with Hoechst 33342 48 hours later and counted, and the data were calculated as for FIG. 9.
Figure 11:
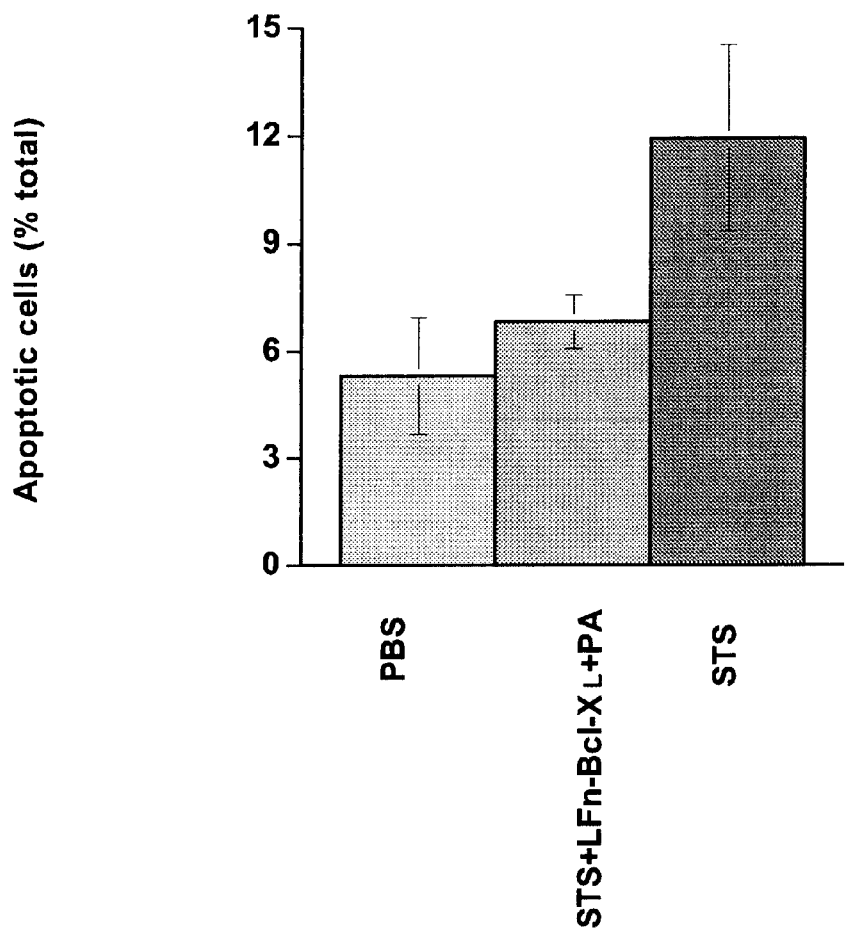
FIG. 11 is a bar graph showing the effect of $LF_n$-Bcl-$x_L$ against Jurkat cells treated with STS. Jurkat cells at $10^5$/ml were treated with 0.1 μM staurosporine alone, 0.1 μM staurosporine along with $LF_n$-Bcl-$x_L$ (28 μg/ml) plus PA (33 μ/ml) or with PBS. The apoptotic and living cells were stained with Hoechest 33342 21 hours later and counted, and the data were calculated as for FIG. 9.

Controls were performed to explore the requirements for apoptosis inhibition. FIG. 10 shows data demonstrating that J774 cells treated with $LF_n$ alone, Bcl-$x_L$ alone, $LF_n$-Bcl-$x_L$ without PA, and PA without $LF_n$-Bcl-$x_L$ were not protected from apoptosis induced by staurosporine, whereas $LF_n$-Bcl-$x_L$ plus PA prevented more than half of the cell death. Jurkat cells were also protected from apoptosis by $LF_n$-Bcl-$x_L$ plus PA (FIG. 11).

This new strategy to block cell death was explored in an in vivo model of neuron apoptosis. Retinal ganglion cells were axotomized and immediately afterwards a mixture containing 0.35 μg of PA and 0.65 μg of $LF_n$-Bcl-$x_L$ was injected into the eye. Control mice were either not axotomized, axotomized and injected with PBS, or axotomized and injected with PA alone. Mice were sacrificed 24 hours later, and the eyes examined histologically. An increase in pyknotic cells, i.e., apoptotic cells (Rabachi et al., *J Neurosci.* 14: 5292–301, 1994), occurs in the ganglion layer 24 hours after axotomy. However, when eyes are injected with $LF_n$-Bcl-$x_L$ and PA, much of the cell death is inhibited. PA alone did not prevent cell death. To quantitate the extent of cell death, the number of living and pyknotic cells in three entire ganglion layers in one eye from each of 4–10 mice was counted. The quantified results are shown in FIG. 12. $LF_n$-Bcl-$x_L$ inhibited more than half of the cell death due to neuron axotomy in vivo.

In view of the many possible embodiments to which the principles of our invention may be applied, it should be recognized that the illustrated embodiments are only preferred examples of the invention, and should not be taken as limitations on its scope. Rather, the scope of the invention is defined by the following claims. We therefore claim as our invention all that comes within the scope and spirit of these claims.

TABLE 2

Inhibition of Apoptosis by Bcl-$x_L$-DTR

| Cell line | Apoptosis inducer | Concentration of Bcl-$x_L$-DTR ($\mu$M) | Time of STS Treatment (Hrs) | Apoptosis Prevention (%*) | DT I0$_{50}$ (M) |
|---|---|---|---|---|---|
| Cos-7 (monkey kidney) | 0.1 $\mu$M STS | 4.8 | 12 | 58.4 | $10^{-12}$–$10^{-11}$ |
| U251 (human glioma) | 0.1 $\mu$M STS | 4.68 | 16 | 57.5 | $10^{-12}$–$10^{-11}$ |
| HeLa (human cervical Ca) | 0.2 $\mu$M STS | 2.17 | 10 | 32.4 | $10^{-12}$–$10^{-11}$ |
| Jurkat (human T leukemia) | 0.1 $\mu$M STS | 4.68 | 12 | 21.2 | $10^{-9}$ |
| 9L (rat gliosarcoma) | 0.1 $\mu$M STS | 4.68 | 12 | -5.4 | >$10^{-7}$ |
| WEHI7.1 (mouse T lymphoma) | 0.1 $\mu$M STS | 4.68 | 12 | 0.5 | >$10^{-7}$ |

*Apoptotic cells were counted with Hoechst dye no. 33342 and the percent prevention from apoptosis was calculated as 1 − (number of apoptotic cells with STS and Bcl-$x_L$-DTR − number of apoptotic cells without STS and Bcl-$x_L$-DTR) / (number of apoptotic cells with STS − number of apoptotic cells without STS and Bcl-$x_L$-DTR) except for the non-adherent Jurkat and WEHI7.1 cells which were counted by trypan blue dye exclusion and % apoptosis prevention calculated as (number of living cells with STS and Bcl-$x_L$-DTR − number of living cells with STS) / (number of living cells without STS and Bcl-$x_L$-DTR).

TABLE 3

Brefeldin A prevents Bcl-$x_L$-DTR blockade of apoptosis

| | PBS | 0.1 $\mu$M STS | 0.1 $\mu$M STS + 2.24 $\mu$M Bcl-$x_L$-DTR | Bcl-$x_L$-DTR |
|---|---|---|---|---|
| Cell death (%) | 1 | 24 | 11 | 56% protection |
| | 2 $\mu$M brefeldin A | 0.1 $\mu$M STS + 2 $\mu$M brefeldin A | 0.1 $\mu$M STS + 2 $\mu$M brefeldin A + 2.24 $\mu$M Bcl-$x_L$-DTR | Bcl-$x_L$-DTR + brefeldin A |
| Cell death (%) | 2 | 35 | 32 | 9% protection |

Apoptotic cells were counted with Hoechst dye no. 33342 14 hours after addition of STS and/or brefeldin A minutes after Bcl-$x_L$-DTR was added to Cos-7 cells. The protection percentage was calculated as 1 − (number of apoptotic cells with STS and Bcl-$x_L$-DTR − number of apoptotic cells without STS and Bcl-$x_L$-DTR) / (number of apoptotic cells with STS − number of apoptotic cells without STS and Bcl-$x_L$-DTR).

We claim:

1. A purified apoptosis-inhibiting fusion protein capable of binding a target cell in vitro, comprising:
   (a) a first domain capable of inhibiting apoptosis in the target cell;
   (b) a second domain capable of specifically targeting the fusion protein to the target cell; and
   (c) a linker connecting the first domain to the second domain, wherein the fusion protein comprises an amino acid sequence as set forth in SEQ ID NO: 2 (Bcl-$x_L$-DTR) and wherein the fusion protein integrates into or otherwise crosses a cellular membrane of the target cell in vitro upon binding.

2. A purified apoptosis inhibiting fusion protein capable of specifically binding a target cell, comprising:
   (a) a first domain capable of inhibiting apoptosis in the target cell; and
   (b) a second domain capable of specifically targeting the fusion protein to the target cell, wherein the fusion protein comprises an amino acid sequence as set forth in SEQ ID NO: 8($LF_n$-Bcl-$x_L$), and wherein the fusion protein integrates into or otherwise crosses a cellular membrane of the target cell upon binding in the presence of protective antigen (PA).

3. The protein of claim 1, wherein the target cell a lymphocyte, an epithelial cell, or a fibroblast.

4. A composition comprising the protein according to claim 1.

5. A composition comprising the protein according to claim 2.

6. A composition comprising the composition according to claim 5, and a pharmaceutically acceptable carrier.

7. A combined composition comprising a fusion protein according to claim 2, and a sufficient amount of protective antigen (PA) to enable measurable transport of the fusion protein into a target cell.

8. The protein of claim 2, wherein the target cell is in vitro.

9. The protein of claim 8, wherein the in vitro target cell is a lymphocyte or a macrophage.

10. The protein of claim 2, wherein the target cell is in vivo.

11. The protein of claim 10, wherein the in vivo target cell is a neuron.

12. The protein of claim 11, wherein the neuron is a retinal ganglion cell.

* * * * *

UNITED STATES PATENT AND TRADEMARK OFFICE
CERTIFICATE OF CORRECTION

PATENT NO. : 6,737,511 B1  
APPLICATION NO. : 09/639245  
DATED : May 18, 2004  
INVENTOR(S) : Youle et al.

It is certified that error appears in the above-identified patent and that said Letters Patent is hereby corrected as shown below:

On the Cover:

| Location: | Error: | Correction: |
|---|---|---|
| References Cited Foreign Patent Documents: | WO 00/45128 | WO 99/45128 |
| References Cited Other Publications page 2, Evan et al. | 281:1371-1322 | 281:1317-1322 |

In the Specification:

| Column/Line: | Error: | Correction: |
|---|---|---|
| 5/28 | cukaryotic | eukaryotic |
| 6/20 | endogencous | endogeneous |
| 6/46 | 1 μμM | 1 μM |
| 6/54 | toy-radiation | to γ-radiation |
| 7/9 | ϖ=0.1 | ⊞ = 0.1 |
| 7/18 | μ/ml | μg/ml |
| 7/39 | Hoechest | Hoechst |
| 9/45 | Bad-DTR | Bad-DTTR |
| 15/5 | Home | Horne |
| 15/13 | thereof | thereof. |
| 20/56 | immediately the last treatment | immediately after the last treatment |
| 21/66 | cancers | cancers). |
| 23/23 | Bad-D1TR | Bad-DTTR |
| 23/32 | Bcl-xi | Bcl-$x_L$ |
| 23/34 | BL2 1 | BL21 |
| 23/45 | μ/ml | μg/ml |
| 24/54 | 53:4701-47 14, | 53:4701-4714, |
| 27/12 | Boc-D-fink | Boc-D-fmk |
| 27/22 | appear, to | appear to |

UNITED STATES PATENT AND TRADEMARK OFFICE
CERTIFICATE OF CORRECTION

PATENT NO. : 6,737,511 B1
APPLICATION NO. : 09/639245
DATED : May 18, 2004
INVENTOR(S) : Youle et al.

It is certified that error appears in the above-identified patent and that said Letters Patent is hereby corrected as shown below:

In the Specification: (cont'd)

| Column/Line: | Error: | Correction: |
| --- | --- | --- |
| 27/34 | Bad-DTR | Bad-DTTR |
| 27/41 | Bad-DTR | Bad-DTTR |
| 27/46 | Bad-DTR | Bad-DTTR |
| 27/49 | Bad-DTR | Bad-DTTR |
| 27/51 | Bad-DTR | Bad-DTTR |
| 27/52 | Bad-DTR | Bad-DTTR |
| 27/58 | Bad-DTR | Bad-DTTR |
| 28/11 | 1995: | 1995; |
| 28/28 | 66.615-619 | 66:615-619 |
| 28/38 | prokarvotic | prokaryotic |
| 29/17 | was | were |

Signed and Sealed this

Thirtieth Day of January, 2007

JON W. DUDAS
*Director of the United States Patent and Trademark Office*